United States Patent
Collinge et al.

(10) Patent No.: US 10,316,099 B2
(45) Date of Patent: Jun. 11, 2019

(54) PRION PROTEIN ANTIBODIES FOR THE TREATMENT OF ALZHEIMER'S DISEASE

(71) Applicant: D-GEN LIMITED, London (GB)

(72) Inventors: John Collinge, London (GB); Andrew J Nicoll, London (GB)

(73) Assignee: D-GEN LIMITED, London (GB)

( * ) Notice: Subject to any disclaimer, the term of this patent is extended or adjusted under 35 U.S.C. 154(b) by 36 days.

(21) Appl. No.: 15/205,649

(22) Filed: Jul. 8, 2016

(65) Prior Publication Data

US 2017/0066833 A1 Mar. 9, 2017

Related U.S. Application Data

(62) Division of application No. 14/118,499, filed as application No. PCT/GB2012/000434 on May 9, 2012, now abandoned.

(30) Foreign Application Priority Data

May 18, 2011 (GB) .................................. 1108490.2

(51) Int. Cl.
*A61K 39/395* (2006.01)
*C07K 16/28* (2006.01)
*A61K 39/00* (2006.01)

(52) U.S. Cl.
CPC ...... *C07K 16/2872* (2013.01); *A61K 39/3955* (2013.01); *A61K 2039/505* (2013.01); *C07K 2317/34* (2013.01); *C07K 2317/76* (2013.01); *C07K 2317/92* (2013.01)

(58) Field of Classification Search
CPC ............ C07K 16/2872; C07K 2317/34; C07K 2317/55; C07K 2317/622; C07K 2317/76; C07K 2317/92
See application file for complete search history.

(56) References Cited

U.S. PATENT DOCUMENTS

| 7,550,144 B2 | 6/2009 | Collinge et al. | |
| 2010/0291090 A1 * | 11/2010 | Strittmatter | C07K 16/2872 424/139.1 |

FOREIGN PATENT DOCUMENTS

| WO | 2004050120 | 6/2004 | |
| WO | WO-2009018625 A1 * | 2/2009 | ....... A61K 39/39558 |

OTHER PUBLICATIONS

Alberts, Bruce et al. Molecular Biology of the Cell, Third Edition. Garland Publishing, Inc., New York, 1994, pp. 1216-1220.*
Cernilec M et al. Identification of an epitope on the recombinant bovine PrP that is able to elicit a prominent immune response in wild-type mice. Immunol. Lett. 2007, 113:29-39.*
Forloni G & Balducci C. Beta-amyloid oligomers and prion protein: Fatal attraction? Prion, Mar. 2011, 5(1):10-15.*
Hampel H et al. The future of Alzheimer's disease: The next 10 years. Prog. Neurobiol. 2011, 95:718-728.*
Kuby Janis, Immunology, Third Edition. WH Freeman & Co., New York 1997, pp. 131-135.*
Lemere CA et al. Amyloid-beta immunotherapy for the prevention and treatment of Alzheimer disease: Lessons from mice, monkeys, and humans. Rejuvenation Res. 2006, 9(1):77-84.*
Vickers JC. A vaccine against Alzheimer's disease: Developments to date. Drugs Aging, 2002, 19(7):487-494.*
Williamson RA et al. Mapping the prion protein using recombinant antibodies. J. Virol. 1998, 72(11):9413-9418.*
White, Anthony R. et al: "Monoclonal antibodies prohibit prion replication and delay the development of prion disease." Nature: International Weekly Journal of Science, Nature Publishing Group, United Kingdom, vol. 422, No. 6927, Mar. 6, 2003, pp. 80-83.
Peretz D et al: "Antibodies inhibit prion propagation and clear cell cultures of prion activity." Nature: International Weekly Journal of Science, Nature Publishing Group, United Kingdom, vol. 412, Aug. 16, 2001, pp. 739-743.
Frier, DB et al: "Interaction between prion protein and toxic amyloid [beta] assemblies can be therapeutically targeted at multiple sites." Nature Communications 2011 Nature Publishing Group GBR, vol. 2, No. 1, 2011.
Chung, E. et al. "Anti-PrPC monoclonal antibody infusion as a novel treatment for cognitive deficits in an Alzheimer's disease model mouse." BMC Neuroscience 11, pp. 130-140 (2010).
Ludwig, Gerald. International Preliminary Report on Patentability, Application No. PCT/GB2012/000434, dated Feb. 14, 2014.

* cited by examiner

*Primary Examiner* — Kimberly Ballard
(74) *Attorney, Agent, or Firm* — Pabst Patent Group LLP

(57) ABSTRACT

The invention relates to a ligand capable of binding PrP at a site within amino acid residues 131 to 153 of PrP, for use in treatment or prevention of impaired synaptic plasticity. The invention also relates to a ligand capable of binding PrP at a site within amino acid residues 131 to 153 of PrP, for use in treatment or prevention of toxicity of Aβ oligomers. The invention also relates to a ligand capable of binding PrP at a site within amino acid residues 131 to 153 of PrP, for use in treatment or prevention of Alzheimer's Disease. The invention also relates to methods of medical treatment.

24 Claims, 16 Drawing Sheets
(1 of 16 Drawing Sheet(s) Filed in Color)
Specification includes a Sequence Listing.

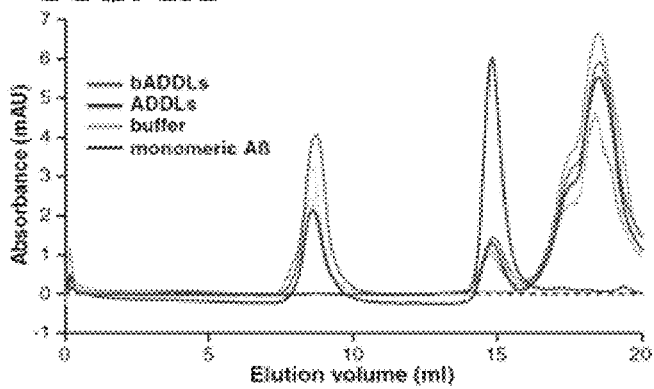
FIG. 1A
FIG. 1B
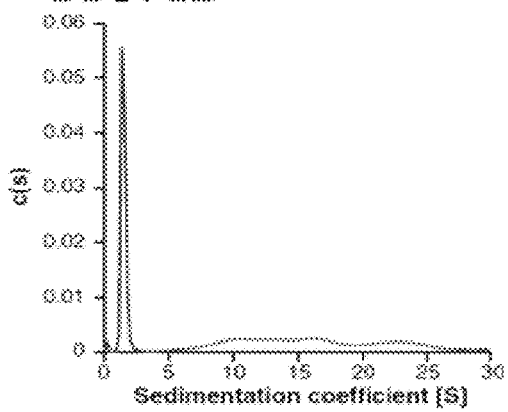
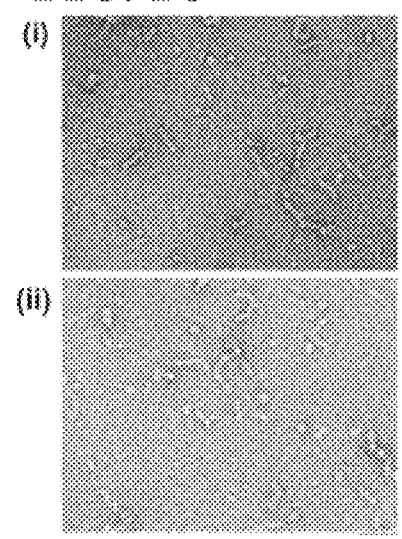
FIG. 1C
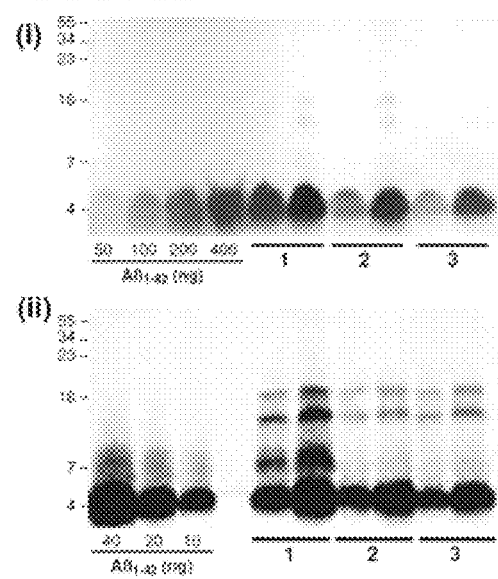
FIG. 1D

FIG. 12A

ICSM181c sequence

```
ATGGATTTACAGGTGCAGATTATCAGCTTCCTGCTAATCAGTGCCTCAGTCATAATATCC   60
                              leader
 M  D  L  Q  V  Q  I  I  S  F  L  L  I  S  A  S  V  I  I  S AGAGGACAAATTGTTCTCACCCAGTCTCCAGCAATCATGTCTGCATCTCCAGGGGAGAAg   120
 leader
 R  G  Q  I  V  L  T  Q  S  P  A  I  M  S  A  S  P  G  E  K GTCACCATGACCTGCAGTGCCAGCTCAAGTGTAAGTTACATGCACTGGTACCAGCAGAAG   180
                              CDR1
 V  T  M  T  C  S  A  S  S  S  V  S  Y  M  H  W  Y  Q  Q  K TCAGGCACCTCCCCCAAAAGATGGATTTATGACACATCCAAACTGGCTTCTGGAGTCCCT   240
                              CDR2
 S  G  T  S  P  K  R  W  I  Y  D  T  S  K  L  A  S  G  V  P GCTCGCTTCAGTGGCAGTGGGTCTGGGACCTCTTACTCTCTCACAATCAGCAGTATGGAG   300
 A  R  F  S  G  S  G  S  G  T  S  Y  S  L  T  I  S  S  M  E GCTGAAGATGCTGCCACTTATTTCTGCCACCAGTGGAGAAgTAACCCATACACGTTCGGA   360
                              CDR3
 A  E  D  A  A  T  Y  F  C  H  Q  W  R  S  N  P  Y  T  F  G GGGGGGACCAAGCTGGAAATAAAACGGGCTGATGCTGCACCAACTGTATCCATCTTCCCA   420
                              Constant Region
 G  G  T  K  L  E  I  K  R  A  D  A  A  P  T  V  S  I  F  P CCATCCAGTGAGCAGTTAACATCTGGAGGTGCCTCAGTCGTGTGCTTCTTGAACAACTTC   480
                   Constant Region
 P  S  S  E  Q  L  T  S  G  G  A  S  V  V  C  F  L  N  N  F TACCCCAAAGACATCAATGTCAAGTGGAAGATTGATGGCAGTGAACGACAAAATGGCGTC   540
                   Constant Region
 Y  P  K  D  I  N  V  K  W  K  I  D  G  S  E  R  Q  N  G  V CTGAACAGTTGGACTGATCAGGACAGCAAAGACAGCACCTACAGCATGAGCAGCACCCTC   600
                   Constant Region
 L  N  S  W  T  D  Q  D  S  K  D  S  T  Y  S  M  S  S  T  L ACGTTGACCAAGGACGAGTATGAACGACATAACAGCTATACCTGTGAGGCCACTCACAAG   660
                   Constant Region
 T  L  T  K  D  E  Y  E  R  H  N  S  Y  T  C  E  A  T  H  K ACATCAACTTCACCCATTGTCAAGAGCTTCAACAGGGGAGAGTGTTAGTGA             711
                   Constant Region
 T  S  T  S  P  I  V  K  S  F  N  R  G  E  C
```

FIG. 12B

ATGGATTTACAGGTGCAGATTATCAGCTTCCTGCTAATCAGTGCCTCAGT
CATAATATCCAGAGGACAAATTGTTCTCACCCAGTCTCCAGCAATCATGT
CTGCATCTCCAGGGGAGAAgGTCACCATGACCTGC<ins>AGTGCCAGCTCAAGT</ins>
<ins>GTAAGTTACATGCAC</ins>TGGTACCAGCAGAAGTCAGGCACCTCCCCAAAAG
ATGGATTTAT<ins>GACACATCCAAACTGGCTTCT</ins>GGAGTCCCTGCTCGCTTCA
GTGGCAGTGGGTCTGGGACCTCTTACTCTCTCACAATCAGCAGTATGGAG
GCTGAAGATGCTGCCACTTATTTCTGC<ins>CACCAGTGGAGAAgTAACCCATA</ins>
<ins>CACG</ins>TTCGGAGGGGGGACCAAGCTGGAAATAAAACGGGCTGATGCTGCAC
CAACTGTATCCATCTTCCCACCATCCAGTGAGCAGTTAACATCTGGAGGT
GCCTCAGTCGTGTGCTTCTTGAACAACTTCTACCCCAAAGACATCAATGT
CAAGTGGAAGATTGATGGCAGTGAACGACAAAATGGCGTCCTGAACAGTT
GGACTGATCAGGACAGCAAAGACAGCACCTACAGCATGAGCAGCACCCTC
ACGTTGACCAAGGACGAGTATGAACGACATAACAGCTATACCTGTGAGGC
CACTCACAAGACATCAACTTCACCCATTGTCAAGAGCTTCAACAGGGGAG
AGTGTTAGTGA

SEQUENCE LISTING

```
<160> NUMBER OF SEQ ID NOS: 6

<210> SEQ ID NO 1
<211> LENGTH: 23
<212> TYPE: PRT
<213> ORGANISM: Homo sapiens

<400> SEQUENCE: 1

Gly Ser Ala Met Ser Arg Pro Ile Ile His Phe Gly Ser Asp Tyr Glu
1               5                   10                  15

Asp Arg Tyr Tyr Arg Glu Asn
            20

<210> SEQ ID NO 2
<211> LENGTH: 208
<212> TYPE: PRT
<213> ORGANISM: Homo sapiens

<400> SEQUENCE: 2

Lys Lys Arg Pro Lys Pro Gly Gly Trp Asn Thr Gly Gly Ser Arg Tyr
1               5                   10                  15

Pro Gly Gln Gly Ser Pro Gly Gly Asn Arg Tyr Pro Pro Gln Gly Gly
            20                  25                  30

Gly Gly Trp Gly Gln Pro His Gly Gly Gly Trp Gly Gln Pro His Gly
        35                  40                  45

Gly Gly Trp Gly Gln Pro His Gly Gly Gly Trp Gly Gln Pro His Gly
    50                  55                  60

Gly Gly Trp Gly Gln Gly Gly Thr His Ser Gln Trp Asn Lys Pro
65                  70                  75                  80

Ser Lys Pro Lys Thr Asn Met Lys His Met Ala Gly Ala Ala Ala Ala
                85                  90                  95

Gly Ala Val Val Gly Gly Leu Gly Gly Tyr Met Leu Gly Ser Ala Met
            100                 105                 110

Ser Arg Pro Ile Ile His Phe Gly Ser Asp Tyr Glu Asp Arg Tyr Tyr
        115                 120                 125

Arg Glu Asn Met His Arg Tyr Pro Asn Gln Val Tyr Tyr Arg Pro Met
    130                 135                 140

Asp Glu Tyr Ser Asn Gln Asn Asn Phe Val His Asp Cys Val Asn Ile
145                 150                 155                 160
```

```
Thr Ile Lys Gln His Thr Val Thr Thr Thr Lys Gly Glu Asn Phe
            165                 170                 175
Thr Glu Thr Asp Val Lys Met Met Glu Arg Val Val Glu Gln Met Cys
        180                 185                 190
Ile Thr Gln Tyr Glu Arg Glu Ser Gln Ala Tyr Tyr Gln Arg Gly Ser
        195                 200                 205
```

<210> SEQ ID NO 3
<211> LENGTH: 405
<212> TYPE: DNA
<213> ORGANISM: artificial
<220> FEATURE:
<223> OTHER INFORMATION: icsm18vh nucleotide sequence

<400> SEQUENCE: 3

```
atggaatgga gctgggtttt cctcttcctc ctgtcaggaa ctgcaggtgt cctctctgag    60
gtccagctac aacagtctgg acctgagctg gtgaagcctg ggtcttcagt gaagatatcc   120
tgcaaggcat ctagaaacac attcactgac tataacttgg actgggtgaa gcagagccat   180
ggaaagacac ttgagtggat tggaaatgtt tatcctaaca atggtgttac tggctacaac   240
cagaagttca gggtaaggc cacactgact gtagacaagt cctccagcac agcctacatg   300
gagctccaca gcctgacatc tgaggactct gcagtctatt actgtgccct ttattactac   360
gatgtctctt actggggcca aggactctg gtcactgtct ctgca              405
```

<210> SEQ ID NO 4
<211> LENGTH: 135
<212> TYPE: PRT
<213> ORGANISM: artificial
<220> FEATURE:
<223> OTHER INFORMATION: icsm18vh aa seq

<400> SEQUENCE: 4

```
Met Glu Trp Ser Trp Val Phe Leu Phe Leu Leu Ser Gly Thr Ala Gly
1               5                  10                  15
Val Leu Ser Glu Val Gln Leu Gln Gln Ser Gly Pro Glu Leu Val Lys
            20                  25                  30
Pro Gly Ser Ser Val Lys Ile Ser Cys Lys Ala Ser Arg Asn Thr Phe
        35                  40                  45
Thr Asp Tyr Asn Leu Asp Trp Val Lys Gln Ser His Gly Lys Thr Leu
    50                  55                  60
Glu Trp Ile Gly Asn Val Tyr Pro Asn Asn Gly Val Thr Gly Tyr Asn
65                  70                  75                  80
Gln Lys Phe Arg Gly Lys Ala Thr Leu Thr Val Asp Lys Ser Ser Ser
                85                  90                  95
Thr Ala Tyr Met Glu Leu His Ser Leu Thr Ser Glu Asp Ser Ala Val
            100                 105                 110
Tyr Tyr Cys Ala Leu Tyr Tyr Tyr Asp Val Ser Tyr Trp Gly Gln Gly
        115                 120                 125
Thr Leu Val Thr Val Ser Ala
    130                 135
```

<210> SEQ ID NO 5
<211> LENGTH: 711
<212> TYPE: DNA
<213> ORGANISM: artificial
<220> FEATURE:
<223> OTHER INFORMATION: ICSM181c nucleotide sequence

<400> SEQUENCE: 5

```
atggatttac aggtgcagat tatcagcttc ctgctaatca gtgcctcagt cataatatcc    60
```

```
agaggacaaa ttgttctcac ccagtctcca gcaatcatgt ctgcatctcc aggggagaag    120
gtcaccatga cctgcagtgc cagctcaagt gtaagttaca tgcactggta ccagcagaag    180
tcaggcacct cccccaaaag atggatttat gacacatcca aactggcttc tggagtccct    240
gctcgcttca gtggcagtgg gtctgggacc tcttactctc tcacaatcag cagtatggag    300
gctgaagatg ctgccactta tttctgccac cagtggagaa gtaacccata cacgttcgga    360
ggggggacca agctggaaat aaaacgggct gatgctgcac caactgtatc catcttccca    420
ccatccagtg agcagttaac atctggaggt gcctcagtcg tgtgcttctt gaacaacttc    480 tacccccaaag acatcaatgt caagtggaag attgatggca gtgaacgaca aaatggcgtc    540
ctgaacagtt ggactgatca ggacagcaaa gacagcacct acagcatgag cagcaccctc    600
acgttgacca aggacgagta tgaacgacat aacagctata cctgtgaggc cactcacaag    660
acatcaactt cacccattgt caagagcttc aacagggag agtgttagtg a              711
```

<210> SEQ ID NO 6
<211> LENGTH: 235
<212> TYPE: PRT
<213> ORGANISM: Artificial
<220> FEATURE:
<223> OTHER INFORMATION: ICSM181c amino acid sequence

<400> SEQUENCE: 6

```
Met Asp Leu Gln Val Gln Ile Ile Ser Phe Leu Leu Ile Ser Ala Ser
 1               5                  10                  15

Val Ile Ile Ser Arg Gly Gln Ile Val Leu Thr Gln Ser Pro Ala Ile
                20                  25                  30

Met Ser Ala Ser Pro Gly Glu Lys Val Thr Met Thr Cys Ser Ala Ser
            35                  40                  45

Ser Ser Val Ser Tyr Met His Trp Tyr Gln Gln Lys Ser Gly Thr Ser
        50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Phe Cys His Gln Trp
            100                 105                 110

Arg Ser Asn Pro Tyr Thr Phe Gly Gly Gly Thr Lys Leu Glu Ile Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Gly Glu Cys
225                 230                 235
```

PRION PROTEIN ANTIBODIES FOR THE TREATMENT OF ALZHEIMER'S DISEASE

FIELD OF THE INVENTION

The invention relates to applications of ligands binding at a specific region of prion protein (PrP) for treating toxicity related to binding of oligomeric Amyloid[beta] to PrP and medical conditions involving same.

BACKGROUND TO THE INVENTION

Prion protein is a well-characterised and studied protein. Major prion protein to (PrP) also known as CD230 (cluster of differentiation 230) is a protein that in humans is encoded by the PRNP gene (PRioN Protein). The major prion protein is expressed in the brain and several other tissues. The human PRNP gene is located on the short (p) arm of chromosome 20 between the end (terminus) of the arm and position 12, from base pair 4,615,068 to base pair 4,630,233. More than 20 mutations in the PRNP gene have been identified in people with inherited prion diseases, which include Creutzfeldt-Jakob disease, Gerstmann-Sträussler-Scheinker syndrome and fatal familial insomnia. Helix 1 is a well characterised alpha-helix within the structure of the $PrP^c$ form of the prion protein (cellular/common form of prion protein). Ligands that bind to helix 1 of the $PrP^c$ are known, for example antibody ICSM-18 as disclosed in WO2004/050120 and commercially available from D-Gen Limited, UK. Soluble non-fibrillar forms of A[beta] have been implicated in, and shown to correlate with, disease progression in animal models of Alzheimer's disease (AD) and patients with AD[9]. Low nanomolar concentrations of synthetic A[beta] are known to disrupt synaptic plasticity in vivo and in vitro, but the conformation and size of the A[beta] species responsible remain unclear[10-13]. It has been reported that the prion protein ($PrP^c$) can act as a cellular receptor for a preparation of synthetic A[beta] referred to as A[beta]-derived diffusible ligands (ADDL) and that $PrP^c$ is required for the disruption of synaptic plasticity mediated by ADDL[1]. Nanomolar affinity of binding has been reported[3,4,14] and a single anti-PrP monoclonal antibody with an epitope around residues 95-105 blocked ADDL binding and toxicity[1]. In further studies, constitutive knock-out of $PrP^c$ expression reversed several pathological phenotypes in a mouse model of AD[2] as did peripheral treatment of the same mouse model with an anti-PrP antibody[15]. Previous work, as disclosed in WO2008/13034, has concentrated on the ADDL binding site of $PrP^c$, which is found at amino acid residues 95-105 of PrP.

Such a finding is of considerable importance given the extensive investigation of targeting $PrP^c$ for prion disease therapeutics[16]. In particular the abolition of neuronal PrP expression in the adult murine nervous system is without serious consequence[17,18] and both small molecule[16] and monoclonal antibody therapeutics[6] have been extensively studied. Indeed therapeutic molecular interactions with $PrP^c$ have been characterised and fully humanised anti-PrP monoclonal antibodies have been produced for clinical studies in human prion disease[8,19].

Using available materials, the ADDL binding site of PrP has been targeted in the prior art.

The present invention seeks to overcome problem(s) associated with the prior art.

SUMMARY OF THE INVENTION

The focus in the art has been on the ADDL binding site of PrP. This is the section of the PrP molecule which is believed to interact with the ADDL. This has therefore been of maximal interest in the field. The binding site on PrP is characterised as being at amino acids 95-105 of PrP. Blocking this site on PrP blocks the interaction with ADDL and ameliorates binding.

In contrast to the prior art, the present inventors have targeted a different part of the PrP molecule. The present inventors have targeted the 131-153 region of PrP. This includes the Helix 1 region of PrP.

It is surprising that targeting this region is effective. Firstly, this region is removed from the established ADDL binding site of PrP. Therefore it would not be expected to be effective in interfering with ADDL binding.

Secondly, this region is at a very distinct spatial site compared to the ADDL binding site. In fact this region is situated at the far opposite side of the three-dimensional PrP molecule. Thus, the site is not only separate in terms of the amino acid residues, but is also separate in three dimensional space.

Therefore, it can be seen that the present invention provides an alternative way of disrupting the ADDL-PrP binding which is different in character to the prior art methods. Moreover, it is itself surprising that it works, since it targets a completely different part of the molecule from the established ADDL binding site.

Thus, in one aspect the invention provides a ligand capable of binding, suitably stably binding, PrP at a site within amino acid residues 131 to 153 of PrP, for use in treatment or prevention of impaired synaptic plasticity.

Suitably the impaired synaptic plasticity is PrP-dependent impaired synaptic plasticity.

In another aspect, the invention relates to a ligand capable of binding, suitably stably binding, PrP at a site within amino acid residues 131 to 153 of PrP, for use in treatment or prevention of toxicity of Aβ oligomers.

In another aspect, the invention relates to a ligand capable of binding, suitably stably binding, PrP at a site within amino acid residues 131 to 153 of PrP, for use in treatment or prevention of Alzheimer's Disease.

Suitably said ligand is an antibody, scFv, or Fab, or other antigen binding fragment thereof.

Suitably said ligand binds PrP at a site within amino acid residues 131 to 153 of PrP with an affinity of 100 nM or less.

Suitably amino acid residues 131 to 153 of PrP have the sequence GSAMSRPIIHFGSDYEDRYYREN (SEQ ID NO. 1).

In another aspect, the invention relates to use of a ligand as described above in the manufacture of a medicament for impaired synaptic plasticity, or toxicity of Aβ oligomers, or Alzheimer's Disease.

In another aspect, the invention relates to a method of treatment of impaired synaptic plasticity, or toxicity of Aβ oligomers, or Alzheimer's Disease, said method comprising administering to a subject a therapeutically effective amount of a ligand as described above.

In another aspect, the invention relates to a method of prevention of impaired synaptic plasticity, or toxicity of Aβ oligomers, or Alzheimer's Disease, said method comprising administering to a subject a therapeutically effective amount of a ligand as described above.

In another aspect, the invention relates to use of a ligand as described above in the manufacture of a medicament for treatment of impaired synaptic plasticity, or toxicity of Aβ oligomers, or Alzheimer's Disease.

In another aspect, the invention relates to use of a ligand as described above in the manufacture of a medicament for prevention of impaired synaptic plasticity, or toxicity of Aβ oligomers, or Alzheimer's Disease.

In another aspect, the invention relates to a method of treatment of impaired synaptic plasticity, or toxicity of Aβ oligomers, or Alzheimer's Disease, said method comprising administering to a subject a therapeutically effective amount of a ligand as described above.

In another aspect, the invention relates to a method of prevention of impaired synaptic plasticity, or toxicity of Aβ oligomers, or Alzheimer's Disease, said method comprising administering to a subject a therapeutically effective amount of a ligand as described above.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 1A-1D—Biophysical characterisation of A[beta] species present in the bADDL preparation FIG. 1A: Size exclusion chromatography of two different batches of freshly prepared ADDLs and bADDLs eluted in PBS showing the ratio of oligomeric (left) to monomeric (middle) A[beta], as well as a buffer peak (right). FIG. 1B: Velocity analytical ultra-centrifugation of freshly prepared bADDLs in Ham's F12 medium as detected by absorbance at 280 nm and represented by c(s), the sedimentation coefficient distribution. The monomer (calculated molecular mass 5,000-6,000) and the oligomer components (calculated molecular mass 90,000-400,000) have been coloured blue and red, respectively. FIG. 1C: Negatively stained transmission electron micrograph of (i) bADDLs and (ii) ADDLs showing a mixture of globular and rod-like structures <100 nm in length. Scale bar 50 nm. FIG. 1D: SDS-PAGE of ADDL preparations analysed by (i) silver staining to estimate the amount of soluble A[beta] present in 3 different ADDL preparations and (ii) Western blot analysis using the N-terminal anti-A[beta] antibody, 6E10, to identify low abundance SDS-stable A[beta] species. Two different concentrations of each test sample (10 microM and 20 microM, for Silver stain and 1 microM and 2 microM for Western blot) were examined

FIG. 3A: Vehicle alone. FIG. 3B: ADDLs contain a mixture of globular structures and flexible protofibrils <100 nm in length. Scale bar used is 100 nm.

FIG. 4A: Extracellular recordings from FVB mice show stable LTP measured up to one hour post-TBS (squares, 184±15%, n=7). Pre-treatment of the slices with bADDLS for 30 min prior to TB caused a significant inhibition of LTP (circles, 109±10%, p<0.01, n=6). FIG. 4B: LTP was reliably induced in slices from PrP null mice treated with vehicle control (squares, 151±8%, n=6). Significantly, perfusion of slices from PrP null mice with the same bADDL preparation used in FIG. 4A did not impair LTP (circles, 149±11%, n=5, P>0.05). FIG. 4C: IP/Western blot analysis of brain extracts revealed the presence of abundant A[beta] monomer and SDS-stable dimer in a sample taken from an AD brain and the complete absence of A[beta] in an extract from a non-demented control subject (Ctrl). Estimates of A[beta] concentration indicate the presence of 14 ng/ml and 3.2ng/ml of monomer and SDS-stable dimer respectively. NS indicates non-specific immunoreactive bands detected when Tris-buffered saline (TBS) alone was immunoprecipitated. Molecular weight markers are on the left. M and D denote A[beta] monomer and SDS-stable dimer. FIG. 4D: Perfusion of slices from wild type FVB mice with AD brain for 30 min prior to TB significantly impaired LTP (circles, 116±9%, n=6) compared to slices perfused with control brain extract (squares, 153±8%, n=6, p<0.05). In contrast, treatment of slices from $PrP^{-/-}$ mice with AD brain extracts failed to alter LTP (triangles, 164±10%, n=6, P>0.05). * refers to when perfusion of bADDLs/AD brain extract was started and arrow denotes application of TB (4 pulses@100 Hz delivered ten times with an inter-train interval of 200 msec). The numbers on the EPSP samples correspond to time during the experiment from which they originate. All values are mean±SEM. Scale bar on insets denotes 1 mv, 5 msec.

Figure 2:
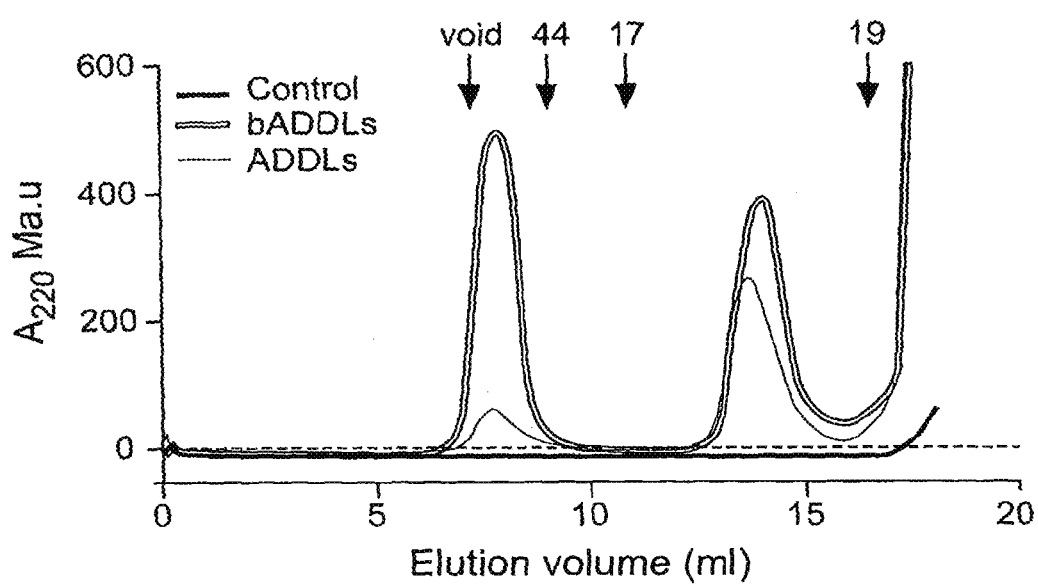
FIG. 2: Size-exclusion chromatography (SEC) profile of both ADDLs and bADDLs ADDLs and bADDLs (1 ml of 100 microM stock) were chromatographed on a Superdex 75 (10/30HR) column and eluted with ACSF at a flow rate of 0.8 ml/min. Peptides were detected by absorbance at 220 nm. The ADDL/bADDL preparations produced two peaks, one eluting in the void volume after 8 ml and the other eluting after 14 ml in a manner highly similar to the freshly dissolved peptide (see FIG. 1B). ADDLs and bADDLs eluted in Ham's F12 medium produced a pattern highly similar to that shown above and in FIG. 1B.
Figure 3A:
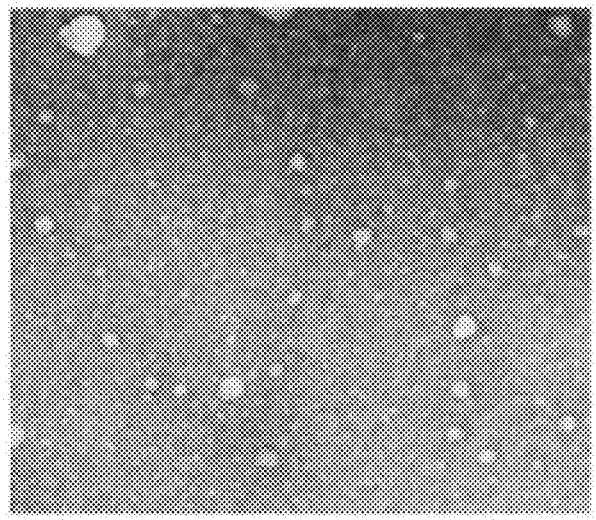
FIGS. 3A-3B: Negatively stained transmission electron micrograph of ADDLs
Figure 3B:

Treatment of C57BL/6J mice with 500 nM bADDLS ([triangle], 94±13%, n=5) and ADDLs ([circle] 115±7%, n=6) produced a significant depression of LTP when compared to controls ([square] 154±6%, n=10, p<0.01). With bADDLs tending to cause a greater depression than ADDLs. This trend may relate to the fact that bADDL preparations tended to have larger amounts of high molecular weight A[beta] species than did ADDLs (FIG. 1B and FIG. 2). * denotes perfusion of ADDLs/bADDLs, arrow denotes theta-burst stimulation.

FIGS. 6A-6F: bADDLs avidly bind PrP in manner that can be blocked by certain anti-PrP antibodies.

Figure 6A:
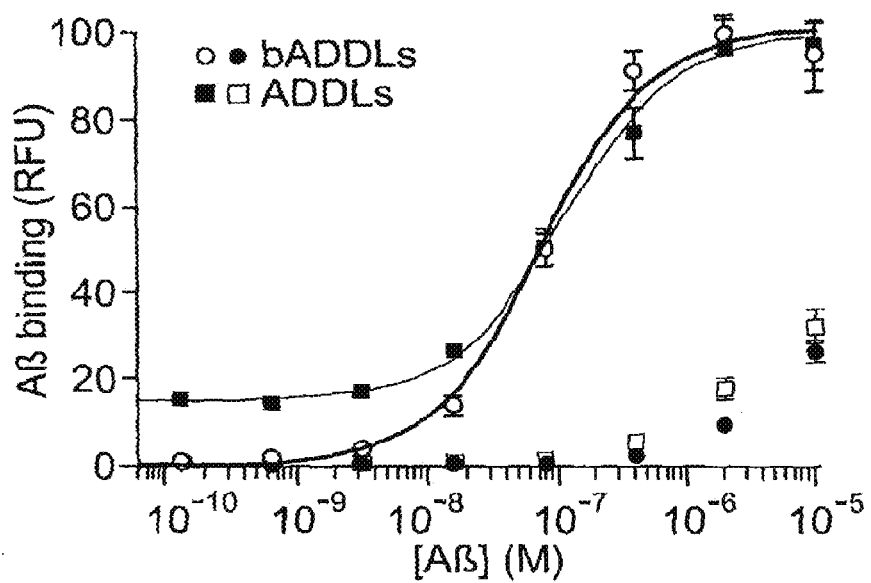
Figure 6B:
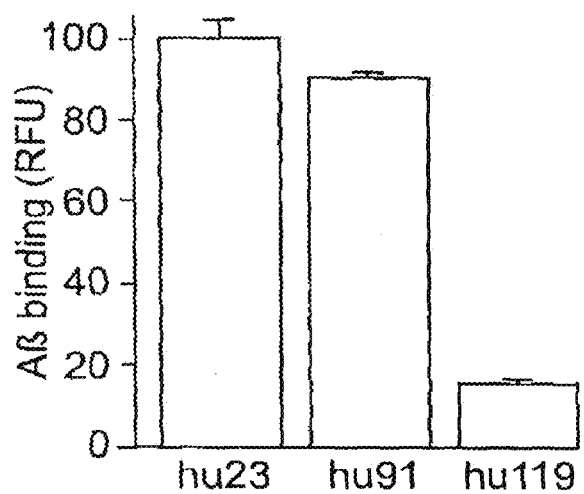
Figure 6C:
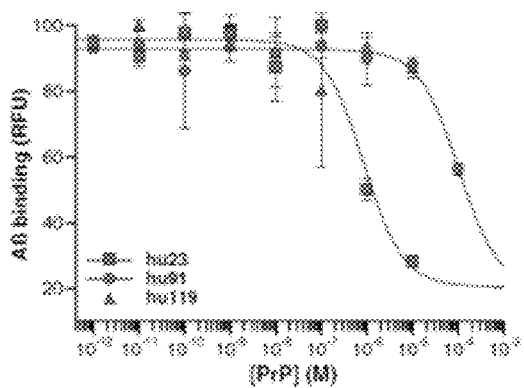
Figure 6D:
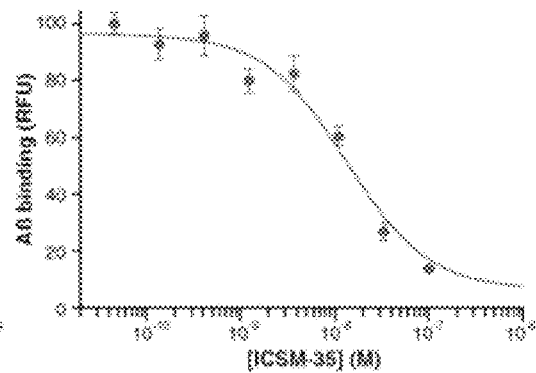
Figure 6E:
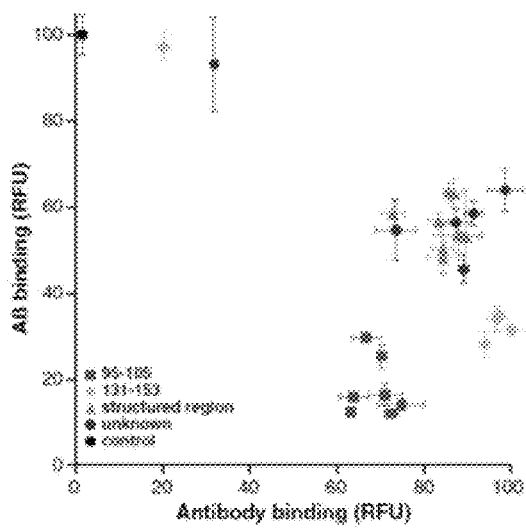
Figure 6F:
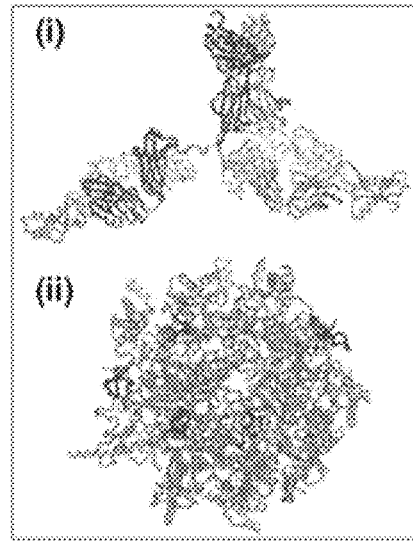

FIG. 6A: Dose response curves of ADDLs (filled in squares) and bADDLs (filled in circles) to plate-bound full-length PrP show both preparations bind to human PrP with apparent dissociation constants of approximately 100 nM. Background wells coated with BSA show the interaction becoming non-specific in the micromolar range. FIG. 6B: At nominal A[beta] concentration of 100 nM a similar level of bADDLs binds to $huPrP_{23-231}$ as to $huPrP_{91-231}$ with background levels binding to $huPrPn_{119-231}$, suggests a single binding site at residues 91-119. FIG. 6C: Competition of binding of bADDLs to surface-bound $huPrP_{23-231}$ by difference constructs of PrP shows that $huPrP_{23-231}$ binds 100-fold tighter to bADDLs in solution than $huPrP_{91-231}$. FIG. 6D: Pre-incubation of surface-bound $huPrP_{23-231}$ with ICSM-35 blocks the subsequent binding of bADDLs in a dose-dependent manner with an $IC_{50}=10.4±1.7$ microM. FIG. 6E: Screen of the ICSM panel of antibodies using a high throughput DELFIA® assay shows that all antibodies that bind to PrP block bADDL binding, with those that recognise an epitope in the region 95-105 (filled in square) inhibiting bADDL binding more than those that recognise an epitope within the region 131-153 (filled in diamond) or those that bind to the structured region (filled in triangle) or undefined epitopes (filled in circle). Surface bound huPrP$_{23-231}$ was pre-incubated for 1 h with 10 nM antibodies and then incubated for 1 h with or without 100 nM bADDLs prior to detection with either Eu-N1 streptavidin or Eu-N1 anti-mouse antibody. FIG. 6F(i): Model of the PrP:ICSM-18 complex based on the published crystal structure and with the antibody extension built in with PrP and the ICSM-18 epitope (yellow)—highlighted; FIG. 6F(ii): Modelled structure of the PrP:A[beta] interaction with A[beta] spheroids (green), PrP (magenta), the ICSM-18 epitope (yellow) and the unstructured ICSM-35 epitope (red) built in, highlighting the large distance between A[beta] binding site and the ICSM-18 epitope. All graphs show Mean±standard deviation and are an average of at least three data points.

Figure 7:
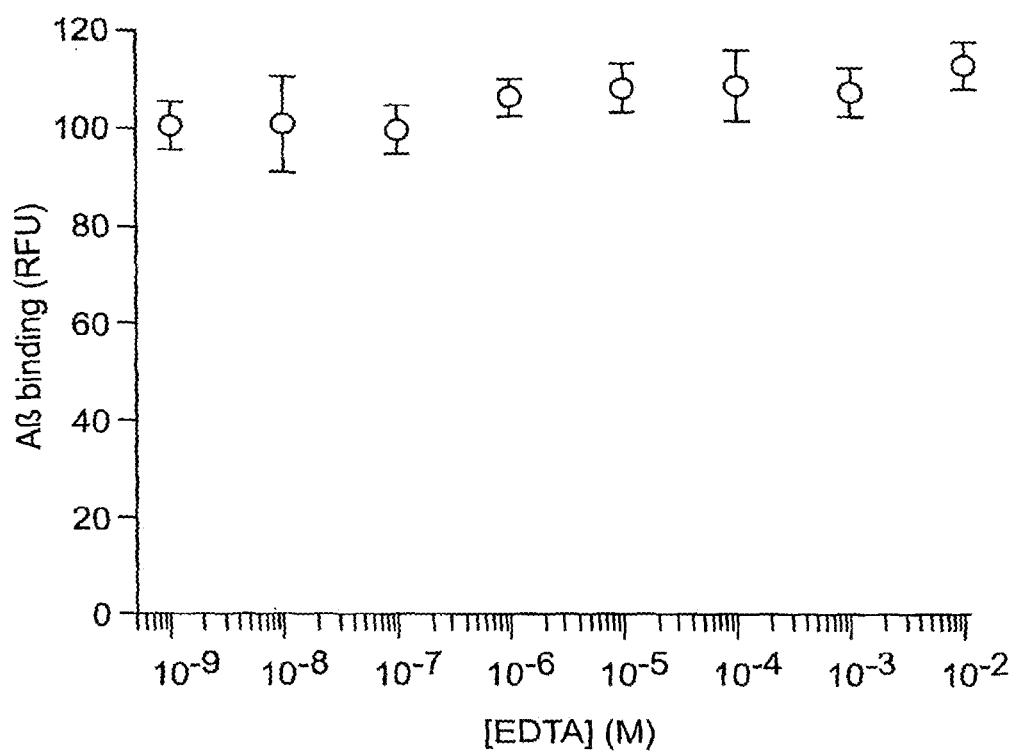

FIG. 7: bADDL binding to huPrP23-231 in the presence of different concentrations of EDTA This demonstrates that the observed interaction between PrP and A[beta] is not caused by copper coordination unless the dissociation constant is tighter than 10-22 M. Binding is shown relative to binding in the absence of EDTA.

Figure 8A:
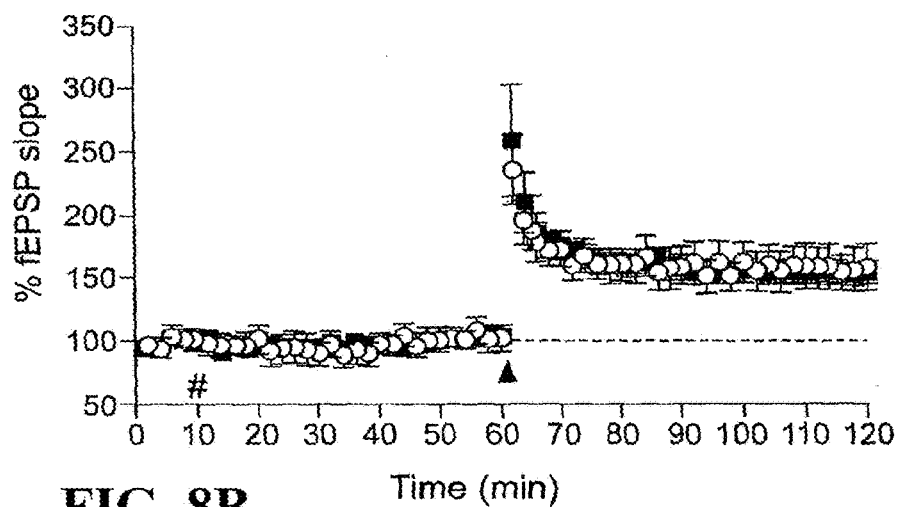
Figure 8B:
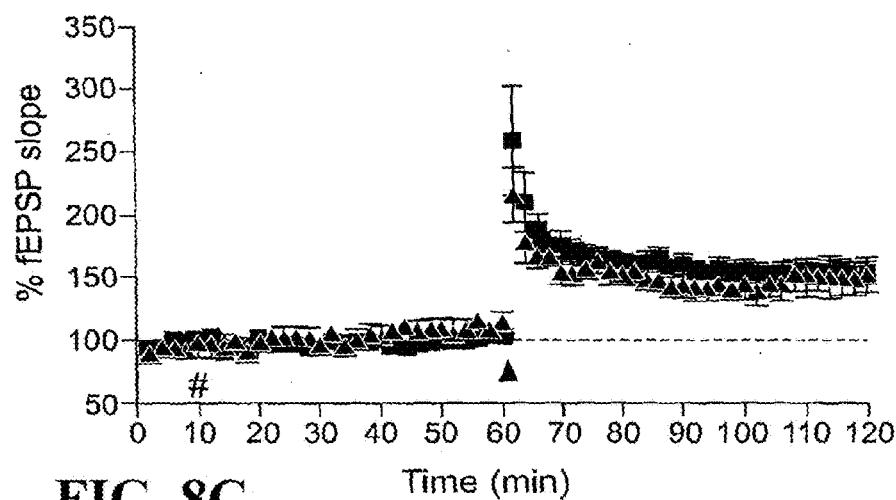
Figure 8C:
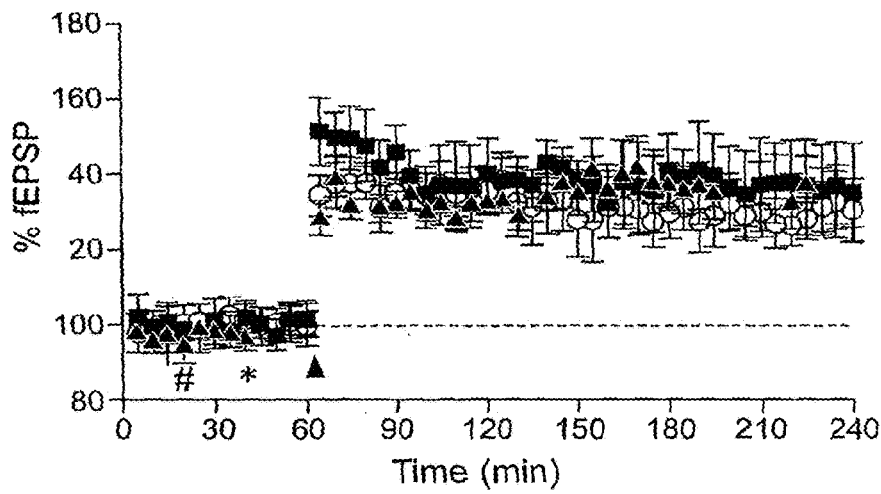

FIGS. 8A-8C: When administered alone neither ICSM-35 nor ICSM-18 alters LTP

FIG. 8A: TB conditioning stimulation in C57/B6 mice treated with 2[micro]g/ml ICSM-35 (circle) induced LTP (157±17%, n=4) that was similar in magnitude to LTP induced in controls (square) (153±7%, n=6). FIG. 8B: Similarly, TB conditioning stimulation in C57BL/6J mice treated with 2[micro]g/ml ICSM-18 (triangle) induced LTP (150±13%, n=3) that was not significantly different from LTP induced in controls (square) (153±7%). FIG. 8C: Injection of ICSM-18 (circle) or an IgG1 isotype control antibody (triangle) i.c.v. (#, both 30[micro]g in 10[micro]l) 30 min before injection of vehicle (*, 5[micro]l i.c.v.) did not significantly affect HFS-induced LTP in the anaesthetised rat (131±9% and 133±7%, respectively; p>0.05 compared with animals that received two (square) vehicle injections, 136±12%, n=3 per group, Mann-Whitney U test). Arrow denotes the time of application of conditioning stimulation.

Figure 9A:
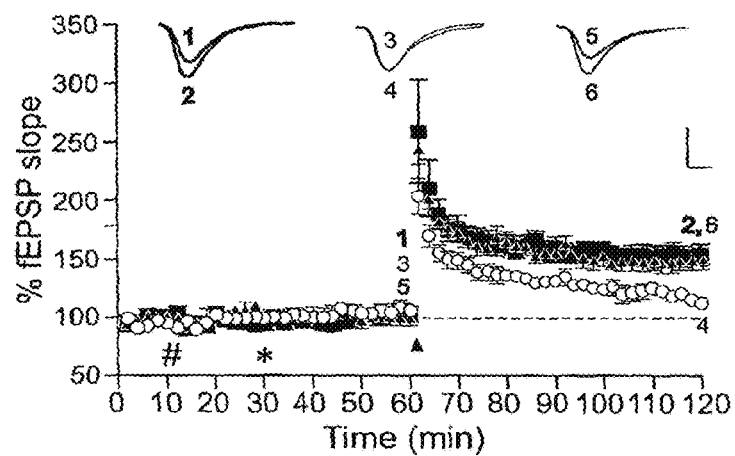
Figure 9B:
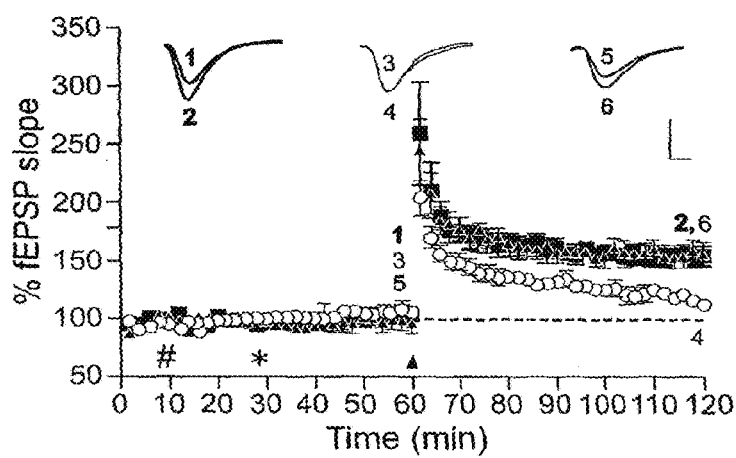
Figure 9C:
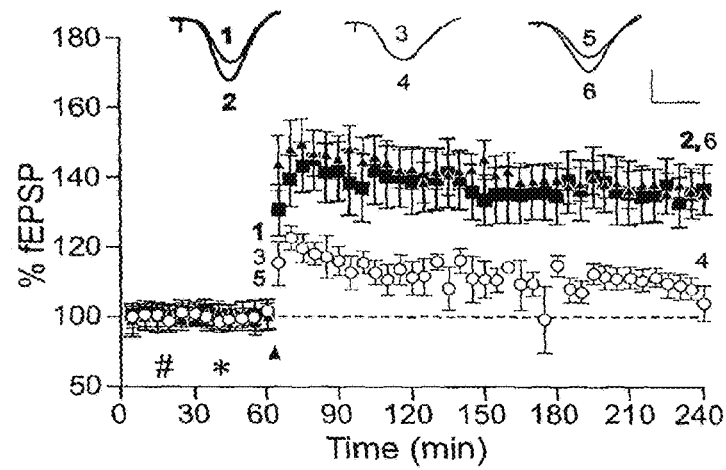

FIG. 9A-9C: Inhibition of LTP by ADDLs or A[beta]-containing AD brain extract is ameliorated by the anti-PrP$^c$ antibodies ICSM-35 and ICSM-18.

FIG. 9A: Conditioning stimulation in hippocampal slices from C57/B6J mice treated with vehicle solution induced a robust LTP (squares, 152±7%, n=6), whereas pre-treatment (30 min) with ADDLs significantly depressed LTP (red circles, 115±5%, n=8, p<0.01). In contrast, perfusion of slices with the anti-PrP antibody, ICSM-35 (which recognises an epitope within residues 93-102) (2 [micro]g/ml), 20 min prior to application of ADDLs prevented the impairment of LTP caused by ADDLs (triangles, 151±9%, n=6, P>0.05). FIG. 9B: As in FIG. 9A above, but ICSM-18 (which recognises an epitope within residues 143-153 of PrP) was used in place of ICSM-35. Like ICSM-35, ICSM-18 (triangles, 157±9%, n=6) completely ameliorated the inhibitory activity of ADDLs (p<0.01). # refers to perfusion of ICSM18/35, * refers to perfusion of ADDLs, arrow denotes TB stimulation. Inset calibration: 1 mV, 5 ms, stimulus artefact was removed for clarity. FIG. 9C: Synaptic field potentials were recorded in vivo from the CA1 area of anaesthetised male Wistar rats. In vehicle-injected rats (#, first injection 10 [micro]l i.c.v.; *, second injection 5 [micro]l 30 min later) high-frequency stimulation (HFS) triggered persistent and stable LTP (squares, 136±7% at 3 h post-tetanus, n=5). In contrast, injection of 5 [micro]l A[beta]-containing brain extract 15 min before HFS, in animals pre-injected with an IgG1 isotype control antibody (30 [micro]g), significantly inhibited LTP (red circles, 106±4%, n=5, p<0.05). Importantly, injection of the anti-PrP$^c$ antibody, ICSM-18 30 min prior to injection of A[beta]-containing TBS AD brain TBS extract (15 min prior to HFS) prevented the inhibition of LTP (grey triangles, 136±5%, n=5). Calibration: 2 mV, 10 msec. # refers to injection of ICSM18, * refers to injection of TBS-extract of human derived A[beta], arrow denotes HFS. Insets show representative electrophysiological traces at the times indicated before (1,3,5) and after (2,4,6) conditioning stimulation.

Figure 10:
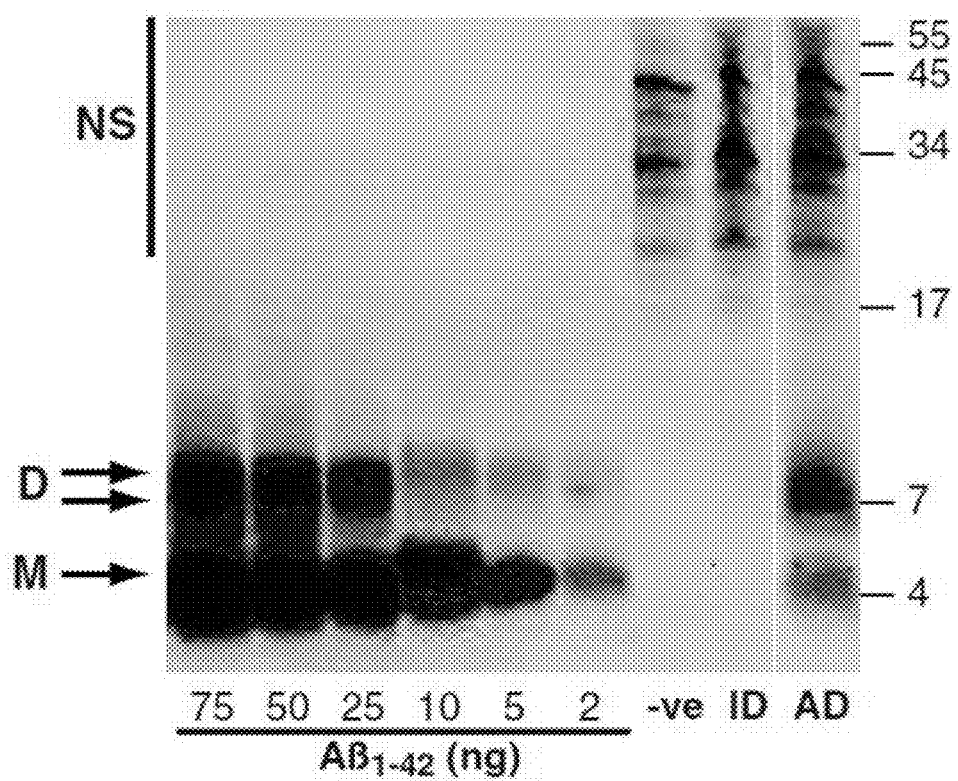

FIG. 10: Characterisation of AD brain extract used for in vivo electrophysiology.

IP/Western blot analysis of brain extracts revealed the presence of abundant A[beta] monomer and SDS-stable dimer in the brain of an 80 year old female diagnosed with Alzheimer's disease (AD) and the complete absence of A[beta] in an immunodepleted (ID) sample of the same brain. NS indicates non-specific immunoreactive bands detected when Tris-buffered saline alone was immunoprecipitated (TBS). Molecular weight markers are on the left. M and D denote A[beta] monomer and SDS-stable dimer. -ve refers to TBS control.

Figure 11:

FIGS. 11, 12A, and 12B each show annotated antibody sequences. Note: boxed residues are CDRs; unboxed, bold is the start of the constant region; regions which are neither leader sequence, constant region nor CDR are defined as framework sequence.

FIG. 11: ICSM18VH sequence (SEQ ID NO. 3).

FIGS. 12A-12B: ICSM18lc sequence (SEQ ID NO. 5).

Figure 13A:
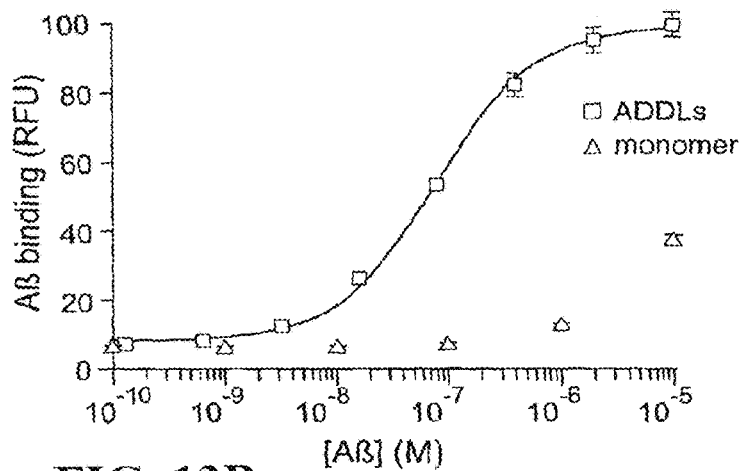
Figure 13B:
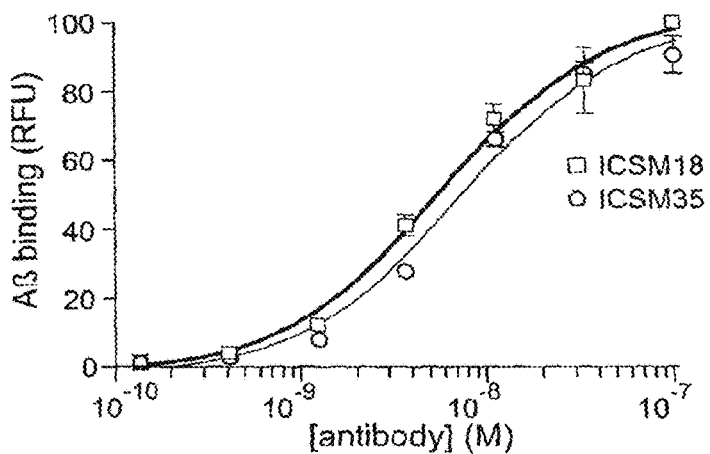
Figure 13C:
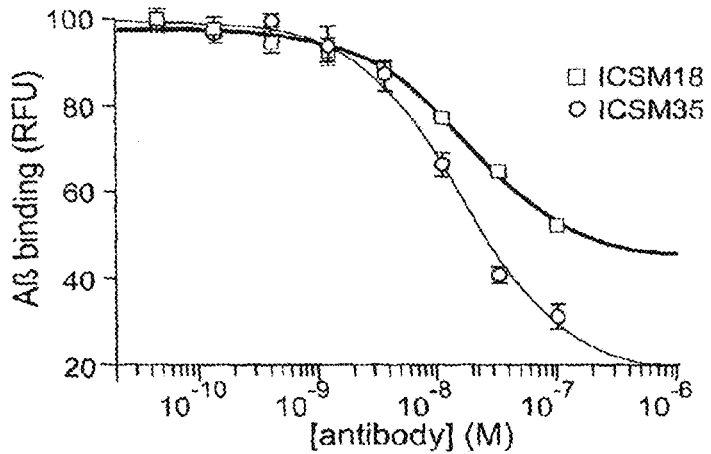

FIGS. 13A-13C: The mode of antibody-induced inhibition of ADDL binding to huPrP$_{23-231}$. FIG. 13A: Relative binding of monomeric (▲) and oligomeric (■) Aβ$_{1-42}$ to surface-bound huPrP$_{23-231}$ detected using 6E10 and DELFIA® Eu-N1 anti-mouse antibodies. FIG. 13B: binding of ICSM-18 (■) and ICSM-35 (●) to surface-bound huPrP$_{23-231}$ detected using 6E10 and DELFIA® Eu-N1 anti-mouse antibodies. FIG. 13C: Inhibition of bADDL binding to surface-bound huPrP$_{23-231}$ by ICSM-18 (■) and ICSM-35 (●) and detected using DELFIA® Eu-N1 streptavidin. Error bars show standard deviations and are the average of at least three replicates.

Figure 14:
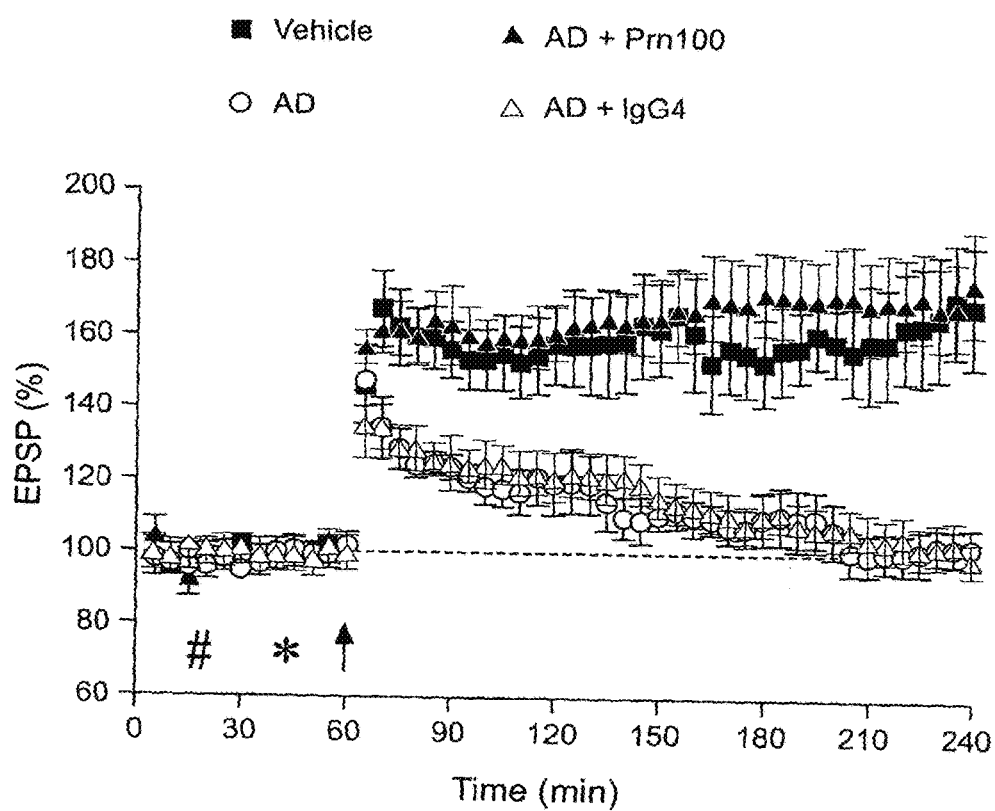

FIG. 14 shows a graph. Synaptic field potentials were recorded in vivo from the CA1 area of anaesthetised male Wistar rats. In vehicle-injected rats (#, first injection 10 [micro]l i.c.v.; *, second injection 5 [micro]l 30 min later) high-frequency stimulation (HFS) triggered persistent and stable LTP (black squares, at 3 h post-tetanus). In contrast, injection of 5 [micro]l A[beta]-containing brain extract 15 min before HFS, in animals pre-injected with an IgG4 isotype control antibody (30 [micro]g), significantly inhibited LTP (pink circles) as did A[beta]-containing brain extract alone (red circles). Importantly, injection of the anti-PrPc antibody, PRN100 30 min prior to injection of A[beta]-containing TBS AD brain TBS extract (15 min prior to HFS) prevented the inhibition of LTP (grey triangles). # refers to injection of PRN100 or control IgG4, * refers to injection of TBS-extract of human derived A [beta], arrow denotes HFS.

DETAILED DESCRIPTION OF THE INVENTION

Definitions

The term 'comprises' (comprise, comprising) should be understood to have its normal meaning in the art, i.e. that the stated feature or group of features is included, but that the term does not exclude any other stated feature or group of features from also being present.

Prion Protein (PrP)

When particular amino acid residues are referred to using numeric addresses, the numbering is taken using human prion protein amino acid sequence as the reference sequence. This is to be used as is well understood in the art to locate the residue of interest. This is not always a strict counting exercise—attention must be paid to the context. For example, if the protein of interest such as human PrP is of a slightly different length, then location of the correct residue in the human sequence corresponding to (for example) residue 131 may require the sequences to be aligned and the equivalent or corresponding residue picked, rather than simply taking the 131st residue of the sequence of interest. This is well within the ambit of the skilled reader.

The reference sequence is suitably amino acid sequence from residue 23 to 231 of human PrP (SEQ ID NO. 2):

```
23KKRPKPGG WNTGGSRYPG QGSPGGNRYP PQGGGGWGQP

HGGGWGQPHG GGWGQPHGGG WGQPHGGGWG QGGGTHSQWN

KPSKPKTNMK HMAGAAAAGA VVGGLGGYML GSAMSRPIIH

FGSDYEDRYY RENM HRYPNQ VYYRPMDEYS NQNNFVHDCV

NITIKQHTVT TTTKGENFTE TDVKMMERVV EQMCITQYER

ESQAYYQRGS 231S
```

Target sequence is marked with underlining/bold. The S1-H1 loop area highlighted by underlining. Helix-1 of PrP is highlighted in bold. This target sequence is well conserved between species.

The prion protein (PrP) has already been well characterised. The prion protein sequence may be derived from the human PRNP gene. More suitably, the protein sequence is the sequence between amino acid residues 23 and 231 as shown above.

Suitably the prion protein to which the ligand according to the invention binds to is PrP$^c$ (cellular/common form prion protein) conformation.

Target Region of PrP

The target region of PrP of maximal interest is the sheet 1-helix 1 loop (the S1H1 loop). This target region suitably comprises helix 1 plus a segment of unstructured sequence. This is sometimes referred to as helix 1 plus the loop between beta strand 1 and alpha helix 1.

More suitably the target region 'comprises helix 1 of PrP. Helix 1 is sometimes defined as including amino acids 143 to 156 of PrP$^c$. More suitably the target region includes aa 143 to 153 or helix 1.

More suitably the target region comprises amino acids 131-153 of PrP.

More suitably the target region may comprise aa 131-150 of PrP, more suitably aa 142-153 of PrP, most suitably aa 136-143 of PrP.

Suitably PrP is PrPc.

PrP may be from any mammalian species such as cow, sheep, mouse, hamster, human or other mammal. Suitably PrP is livestock or human PrP. Suitably PrP is human PrP.

Suitably the target region excludes the ADDL binding site aa 95-105 of PrP, which has been described in the art as acknowledged herein. The invention is different from this because a target site separate and distinct from the ADDL binding site is targeted herein. Suitably the target site does not comprise aa 95-105 of PrP. Suitably the target site does not overlap with aa 95 to 105 of PrP.

Mutation

Mutating has it normal meaning in the art and may refer to the substitution or truncation or deletion of the residue, motif or domain referred to. Mutation may be effected at the polypeptide level e.g. by synthesis of a polypeptide having the mutated sequence, or may be effected at the nucleotide level e.g. by making a nucleic acid encoding the mutated sequence, which nucleic acid may be subsequently translated to produce the mutated polypeptide. Where no amino acid is specified as the replacement amino acid for a given mutation site, suitably alanine (A) is used.

Conservative substitutions may be made, for example according to the Table below. Amino acids in the same block in the second column and preferably in the same line in the third column may be substituted for each other:

| ALIPHATIC | Non-polar | G A P M |
|           |           | I L V |
|           | Polar - uncharged | C S T |
|           |           | N Q |
|           | Polar - charged | D E |
|           |           | K R |
| AROMATIC  |           | H F W Y |

Fragment

A fragment is suitably at least 10 amino acids in length, suitably at least 25 amino acids, suitably at least 50 amino acids, suitably at least 100 amino acids, suitably at least 200 amino acids, suitably the majority of the polypeptide of interest. Suitably a fragment comprises a whole motif or a whole domain of the polypeptide of interest.

Sequence Homology/Identity

Although sequence homology can also be considered in terms of functional similarity (i.e., amino acid residues having similar chemical properties/functions), in the context of the present document it is preferred to express homology in terms of sequence identity.

Sequence comparisons can be conducted by eye or, more usually, with the aid of readily available sequence comparison programs. These publicly and commercially available computer programs can calculate percent homology (such as percent identity) between two or more sequences.

Percent identity may be calculated over contiguous sequences, i.e., one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example in an otherwise identical pair of sequences, one insertion or deletion will cause the following amino acid residues to be put out of alignment, thus potentially resulting in a large reduction in percent homology (percent identity) when a global alignment (an alignment across the whole sequence) is performed. Consequently, most sequence comparison methods are designed to produce optimal alignments that take into consideration possible insertions and deletions without penalising unduly the overall homology (identity) score. This is achieved by inserting "gaps" in the sequence alignment to try to maximise local homology/identity.

These more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum percent homology therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package, FASTA (Altschul et al., 1990, J. Mol. Biol. 215: 403-410) and the GENEWORKS suite of comparison tools.

Although the final percent homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied. It is preferred to use the public default values for the GCG package, or in the case of other software, the default matrix, such as BLOSUM62. Once the software has produced an optimal alignment, it is possible to calculate percent homology, preferably percent sequence identity. The software typically does this as part of the sequence comparison and generates a numerical result.

In the context of the present document, a homologous amino acid sequence is taken to include an amino acid sequence which is at least 15, 20, 25, 30, 40, 50, 60, 70, 80 or 90% identical, preferably at least 95 or 98% identical at the amino acid level. Suitably said comparison is made over at least 50 or 100, preferably 200, 300, 400 or 500 amino acids with any one of the relevant polypeptide sequences disclosed herein, most suitably across the full length of the polypeptide of interest. Suitably, homology should be considered with respect to one or more of those regions of the sequence known to be essential for protein function rather than non-essential neighbouring sequences. This is especially important when considering homologous sequences from distantly related organisms.

The same considerations apply to nucleic acid nucleotide sequences.

The term 'derived from' has its normal meaning in the art, wherein a substance is considered to be 'derived from' a first substance when part of the substance has been created or constructed through a chain of events which incorporates all or part of the first substance into the substance in question. Naturally the two substances are likely to differ e.g. through mutation, addition or deletion or similar modification, but if the substance in question has inherited features from the first substance then it is derived from it. In particular, when used in connection with biopolymers such as polynucleotide(s) or polypeptide(s), a substance is considered to be derived from a first substance when it possesses sufficient sequence identity to be recognised as related to the first substance. In this context, if a substance is derived from a first substance, then said substance preferably has at least 10 contiguous residues which possess at least 25% identity with the first substance, preferably 30% identity, preferably 40% identity, preferably 50% identity, preferably 60% identity, preferably 70% identity, preferably 80% identity, preferably 90% identity, preferably 95% identity, preferably 96% identity, preferably 97% identity, preferably 98% identity, preferably 99% identity or even more. Preferably said substance has at least 15 contiguous residues with said identity, preferably at least 20 residues, preferably at least 30 residues, preferably at least 50 residues, preferably at least 100 residues, preferably at least 200 residues, or even more. For multimeric entities, the term may be applied to the complex and/or to individual components as will be apparent from the context. Generally it will be enough if one of the subunits is derived from the given entity.

Abeta

A[beta] oligomerisation can have deleterious effects. Abeta oligomerisation is implicated in various medical conditions, and the uses and methods described advantageously counteract such conditions.

Thus the invention relates to the treatment and/or prevention of medical condition(s) linked to A[beta] oligomerisation. Examples of these include Lewy body dementia and inclusion body myositis. Abeta oligomerisation can take the form of plaque formation. An important medical condition involving plaque formation is Alzheimer's Disease (AD).

A[beta]-derived diffusible ligands (ADDL) are synthetic soluble oligomeric non-fibrillar forms of A[beta] (monomer) which can be used to study A[beta] oligomerisation. ADDL inhibits long term potentiation (LTP). LTP is connected with synaptic plasticity. Thus the invention finds application in medical conditions which manifest abnormal synaptic plasticity such as impaired synaptic plasticity. Synaptic plasticity is the ability of the synapse between two neurons to change in strength in response to either use or disuse of transmission over synaptic pathways. Medical conditions that manifest abnormal synaptic plasticity include cognitive maladies such as Alzheimer's Disease.

Suitably the ligand according to the invention is for use in preventing or treating medical conditions linked to A[beta] oligomerisation, more suitably the medical condition is Alzheimer's Disease (AD).

AD is a heterogeneous disease and may be considered a clinicopathological syndrome. As such, a number of studies have reported deleterious effects of A[beta] that do not require PrP expression[3-5]. In this context it is important to recognise that a range of different A[beta] preparations have been used and that this may in part explain some of the conflicting reports. Moreover, discrepancies between animal, tissue, cellular and biochemical AD models with respect to a possible role for $PrP^c$ are to be anticipated. Even given that $PrP^c$ is an important receptor for toxic A[beta] species, it would not be expected that $PrP^c$ ablation would rescue all aspects of pathology in each model. Further, given that the concentration of the active species causing disease in the studies is not always known and may differ between studies by different groups some effects may be due to higher A[beta] concentrations which could elicit non-specific toxic effects. Without wishing to be bound by theory, suitably when the invention is applied to AD or Abeta toxicity, the AD or Abeta toxicity is PrP-mediated AD or Abeta toxicity.

Ligands

PrP binding ligands of the invention are suitably ligands binding the target region of PrP as described, suitably binding the target region of PrP$^c$ as described.

The ligand may be a single entity or it may be a combination of entities. Suitably it is a single entity.

The ligand may be an organic compound or other chemical, whether natural or artificial. The ligand may be an amino acid molecule, a polypeptide, or a chemical derivative thereof, or a combination thereof. The ligand may be designed or obtained from a library of compounds, which may comprise peptides, as well as other compounds, such as small organic molecules. By way of example, the ligand may be a natural substance, a biological macromolecule, or an extract made from biological materials such as bacteria, fungi, or animal (particularly mammalian) cells or tissues, an organic or an inorganic molecule, a synthetic agent, a semi-synthetic agent, a to structural or functional mimetic, a peptide, a peptidomimetic, a derivatised agent, a peptide cleaved from a whole protein, or a peptide synthesised synthetically (such as, by way of example, either using a peptide synthesiser or by recombinant techniques or combinations thereof, a recombinant ligand, an antibody, a natural or a non-natural ligand, a fusion protein or equivalent thereof and mutants, derivatives or combinations thereof).

Ligands that bind to the target region of PrP are known in the art.

The ligand may be a protein. One example of such a ligand is Tetraspanin-7.

Suitably the ligand may be an antibody, or an antibody derivative such as a scFv, or Fab. The term "antibody" as used herein is also intended to encompass antibodies, digestion fragments, portions or variants thereof, including antibody mimetics, or comprising portions of antibodies that mimic the structure and/or function of an antibody or fragment or portion thereof, including single chain antibodies and fragments thereof. The important function to be preserved in each case is recognition of (i.e. effective binding to) the target region of PrP. Typically this recognition/binding function is mediated by the complementarity determining regions (CDRs) of the antibody. Thus suitably the ligand of the invention or fragment thereof comprises CDRs recognising the target region of PrP. Functional fragments include antigen binding fragments that bind to the target region of PrP$^c$. For example, antibody fragments capable of binding including, but not limited to Fab (e.g., by papain digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the present invention. Antibody fragments are also intended to include, e.g., domain deleted antibodies, diabodies, linear antibodies, single-chain antibody molecules, and multispecific antibodies formed from antibody fragments.

Examples of antibodies that bind the target region of PrP are known in the art. Examples include ICSM17 (for aa residues 131-150; available from D-Gen Ltd, UK), ICSM18 (for aa residues 142-153; available from D-Gen Ltd, UK), ICSM 30 (for aa residues 136-143; available from D-Gen Ltd, UK) and ICSM 31 (for aa residues 136-143; available from D-Gen Ltd, UK).

ICSM 32 (131-150; available from D-Gen Ltd, UK) also this spans the target region.

Antibody Sha31 (Medicorp Inc.; Alier et al 2011 J. Neurosci. vol 31 pages 16292-16297) binds to residues 145-152 of PrP and therefore also binds within the target region. Sha31antibody is available from Bertin Pharma (subsidiary of Bertin Technologies), France, as product number A03213.

Other known helix-1 binding antibodies (for example, 6H4 (e.g. from Prionics AG, Wagistrasse 27a, CH-8952 Schlieren-Zurich, Switzerland); E12/2 (e.g. as published in Cernilec et al 2007 Immunol Lett. October 31;vol 113(1) pages 29-39. Epub 2007 Aug. 20.); D18 e.g. as published in Peretz et al 2001 Nature vol 412, pages 739-743) may find application in the invention.

A preferred example of such an antibody is ICSM-18 as used in the Examples below. More suitably such an antibody is a humanised version of ICSM-18 such as PRN100.

The antibodies may be in any suitable form known in the art for therapeutic use. The antibodies may be whole or fragments thereof.

In more detail, Suitably the ligand may be an antibody, or an antibody derivative such as a scFv, or Fab. The term "antibody" as used herein is intended to encompass "immunoglobulins" and derivatives thereof. Immunoglobulins comprise various broad classes of polypeptides that can be distinguished biochemically. In many examples, immunoglobulins consist of combination heavy chains and light chains. All immunoglobulin classes including IgM, IgA, IgD, IgE, IgG and IgY and where appropriate, their subclasses, are clearly within the scope of the present invention. The following discussion will generally be directed to the IgG class of immunoglobulin molecules. With regard to IgG, a standard immunoglobulin molecule comprises two identical light chain polypeptides of molecular weight approximately 25 kDa, and two identical heavy chain polypeptides of approximate molecular weight 50 kDa. The resulting molecule, which is conventionally referred to as an IgG "monomer" consists of identical halves and the four chains that are typically joined by disulfide bonds in a "Y" configuration wherein the light chains adjoin the heavy chains starting at the mouth of the "Y" and continuing through the variable region or domain. It is well recognised by those skilled in the art that immunoglobulins can be characterised in terms of variable and constant domains. In this regard, it will be appreciated that the variable domains of both the light (VL) and heavy (VH) chain portions determine antigen recognition and specificity. Conversely, the constant domains of the light chain (CL) and the heavy chain (normally consisting of CH1, CH2 or CH3 domains) confer important biological properties such as secretion, transplacental mobility, Fc receptor binding, complement binding, and the like. As indicated above, the variable region allows the antibody to selectively recognize and specifically bind epitopes on antigens. That is, the VL domain and VH domain of an antibody combine to form the variable region that defines a three dimensional antigen binding site, this site is also called the "antigen receptor". This antibody structure forms the antigen binding site or antigen receptor present at the end of each arm of the Y. More specifically, the antigen binding site is defined by three complementarity determining regions (CDRs) on each of the VH and VL chains. Thus within the amino acid sequence of a variable domain of an antibody there are three CDRs (known as CDR1, CDR2 and CDR3). Since most sequence variation associated with immunoglobulins is found in the CDRs, these regions are sometimes referred to as "hypervariable regions", among these CDRs, CDR3 shows the greatest variability. Since the antigen binding sites are typically composed of two variable domains (on two different polypeptide chains being the heavy and light chain), there are six CDRs for each antigen receptor that can collectively come into contact with the antigen. Thus a single IgG molecule has two antigen receptors, and therefore consists of twelve CDRs. CDRs can also be referred to as "idiotypes". In some instances, for example certain immunoglobulin molecules derived from camelid species or engineered molecules based on camelid immunoglobulins, a complete immunoglobulin molecule may consist of heavy chains only, with no light chains. See, e.g., Hamers Casterman et al, Nature 363:446 448 (1993).

The ligand may be an antigen binding molecule, such as in one embodiment, an antigen binding molecule of the invention comprises at least one heavy or light chain CDR of an antibody molecule. In another embodiment, an antigen binding molecule of the invention comprises at least two CDRs from one or more antibody molecules. In another embodiment, an antigen binding molecule of the invention comprises at least three CDRs from one or more antibody molecules, in another embodiment, an antigen binding molecule of the invention comprises at least four CDRs from one or more antibody molecules. In another embodiment, an antigen binding molecule of the invention comprises at least five CDRs from one or more antibody molecules. In another embodiment, an antigen binding molecule of the invention comprises at least six CDRs from one or more antibody molecules. Antibodies or immunospecific fragments thereof for use in the methods of the invention include, but are not limited to, polyclonal, monoclonal, multispecific, human, humanized, primatized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to binding molecules disclosed herein). ScFv molecules are known in the art and are produced using recombinant DNA technology as described in the Winter patent (ref). Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule. The term "antibody" as used herein is also intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof; each containing at least one CDR. See Qiu et al., Nature Biotechnology, 25:921-929 (2007). Functional fragments include antigen binding fragments that bind to a PrPC antigen. For example, antibody fragments capable of binding to PrP or a portion thereof, including, but not limited to Fab (e.g., by papain digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the present current invention. Antibody fragments are also intended to include for example, domain deleted antibodies, linear antibodies, single-chain antibody molecules, multispecific antibodies formed from antibody fragments and diabodies. Diabodies are formed by the creation of scFvs with linker peptides that are too short for the two variable regions to fold together (about five amino acids), forcing scFvs to dimerize. Diabodies have been shown to have dissociation constants up to 40-fold lower than corresponding scFvs, meaning that they have a much higher affinity to their target. Consequently, drugs based on diabodies could in principle be used at much lower doses than other therapeutic antibodies.

Modified versions of each of these categories of recombinant antibody fragments and combinations thereof will be discernible to the skilled person and are within the scope of the current invention. Antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. Antibodies or immunospecific fragments thereof for use in the therapeutic methods disclosed herein may be from any animal origin including birds and mammals. Preferably, the antibodies are human, murine, donkey, rabbit, goat, guinea pig, camel, llama, horse, or chicken antibodies. In another embodiment, the variable region may be chondrichthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described below and, for example in, U.S. Pat. No. 5,939,598 by Kucherlapati et al. In certain PrPC antibodies or immunospecific fragments thereof for use in the treatment methods disclosed herein, the heavy chain portions of one polypeptide chain of a multimer are identical to those on a second polypeptide chain of the multimer. Alternatively, heavy chain portion-containing monomers for use in the methods of the invention are not identical.

For example, each monomer may comprise a different target binding site, forming, for example, a bispecific antibody.

The antibodies may be humanised. Humanisation of antibodies is known in the art and can be easily accomplished by the skilled worker. For example, ICSM18 may be advantageously humanised with reference to the sequences encoding the CDRs. Suitably the antibody comprises at least the CDRs of one or more antibodies described herein.

In this regard, the following nucleotide sequence corresponds to ICSM18VH (SEQ ID NO. 3):

```
ICSM18VH
ATGGAATGGAGCTGGGTTTTCCTCTTCCTCCTGTCAGGAACTGCAGGTGT

CCTCTCTGAGGTCCAGCTACAACAGTCTGGACCTGAGCTGGTGAAGCCTG

GGTCTTCAGTGAAgATATCCTGCAAGGCATCTAGAAACACATTCACTGAC

TATAACTTGGACTGGGTGAAGCAGAGCCATGGAAAGACACTTGAGTGGAT

TGGAAATGTTTATCCTAACAATGGTGTTACTGGCTACAACCAgAAgTTCA

GGGGTAAGGCCACACTGACTGTAgACAAGTCCTCCAGCACAGCCTACATG

GAGCTCCACAGCCTGACATCTGAGGACTCTGCAGTCTATTACTGTGCCCT

TTATTACTACgATgTCTCTTACTGGGGCCAAGGGACTCTGGTCACTGTCT

CTGCA
```

The following nucleotide sequence corresponds to ICSM181c (SEQ ID NO. 5):

```
ICSM181c
ATGGATTTACAGGTGCAGATTATCAGCTTCCTGCTAATCAGTGCCTCAGT

CATAATATCCAGAGGACAAATTGTTCTCACCCAGTCTCCAGCAATCATGT
```

```
-continued
CTGCATCTCCAGGGGAGAAgGTCACCATGACCTGCAGTGCCAGCTCAAGT

GTAAGTTACATGCACTGGTACCAGCAGAAGTCAGGCACCTCCCCCAAAAG

ATGGATTTATGACACATCCAAACTGGCTTCTGGAGTCCCTGCTCGCTTCA

GTGGCAGTGGGTCTGGGACCTCTTACTCTCTCACAATCAGCAGTATGGAG

GCTGAAGATGCTGCCACTTATTTCTGCCACCAGTGGAGAAgTAACCCATA

CACGTTCGGAGGGGGGACCAAGCTGGAAATAAAACGGGCTGATGCTGCAC

CAACTGTATCCATCTTCCCACCATCCAGTGAGCAGTTAACATCTGGAGGT

GCCTCAGTCGTGTGCTTCTTGAACAACTTCTACCCCAAAGACATCAATGT

CAAGTGGAAGATTGATGGCAGTGAACGACAAAATGGCGTCCTGAACAGTT

GGACTGATCAGGACAGCAAAGACAGCACCTACAGCATGAGCAGCACCCTC

ACGTTGACCAAGGACGAGTATGAACGACATAACAGCTATACCTGTGAGGC

CACTCACAAGACATCAACTTCACCCATTGTCAAGAGCTTCAACAGGGGAG

AGTGTTAGTGA
```

FIG. 11 and FIG. 12 show preferred antibody sequences which have been annotated to show the CDRs and other features.

Guidance regarding humanisation may be found for example in the literature as published by Greg Winter et al., and techniques for the manipulation and production of recombinant antibodies may be found in Harlow and Lane 'Antibodies-A Laboratory Manual', Cold Spring Harbour press.

In one embodiment, the antibodies (or fragments) may advantageously be humanised by manufacture of chimaeric antibodies.

In another embodiment, the antibodies (or fragments) may advantageously be CDR-grafted.

In another embodiment, the antibodies (or fragments) may advantageously be fully humanised to the extent that the technology permits.

Binding Affinity

By binding affinity is meant the affinity of binding of the ligand to the PrP molecule.

As will be appreciated by the skilled reader, high affinity means a low dissociation constant (Kd). In other words 'tighter' binding antibodies saturate the target sequence at a lower concentration than 'weaker' binding antibodies. Thus the tighter binding antibodies have a lower dissociation constant (Kd). Thus an antibody with 'higher affinity' in common parlance is a tighter binding antibody with a lower dissociation constant (Kd) value.

The ligand needs to have a high enough affinity (i.e. a low enough Kd) for the target sequence of PrP to remain stably bound. For example, ICSM 32 (136-143) recognises the target sequence of PrP but did not inhibit binding to Abeta because it did not remain stably bound to PrP during the experiment. Thus, the affinity of the ligand is suitably 100 nM or less. More suitably the affinity of the ligand is 10 nM or less such as 1-10 nM. More suitably the affinity of the ligand is 1 nM or less such as 1 nM to 100 pM. Most suitably the affinity is approximately 600 pM, which is the affinity of ICSM18 (equivalent humanised version is PRN100).

Binding affinity can be measured according to any suitable method known in the art. For example, affinity values may be determined by following the method given in the examples, for example under the heading 'DELFIA® Assay' and subheading 'Antibody Binding (Affinity) Determination'.

Suitably the ligand such as antibody specifically binds to the target sequence of PrP. A ligand such as antibody "specifically binds" to the target sequence of PrP if reacts at a detectable level with the target sequence of PrP, and does not react detectably with peptides containing an unrelated or different sequence. Binding properties may be assessed as described.

Administration/Formulation

Methods of administering the ligands that target prion proteins for inhibition of oligomeric A[beta] binding, and for other diseases involving prion proteins in the nervous system, are well known in the art and incorporated herein as methods of administering the ligands according to the invention. Compositions involving the ligands of the invention are also well-known in the art and incorporated herein by reference for use in preventing or treating medical conditions linked to A[beta] oligomerisation.

The ligand used in the methods of the invention may be formulated into pharmaceutical compositions for administration to mammals, including humans. The pharmaceutical compositions, which may be used in the methods of this invention, may comprise one or more pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and/or wool fat. The compositions used in the methods of the present invention may be administered by any suitable method, e.g., parenterally, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Ligands used in the methods of the invention may act in the nervous system to inhibit suppression of long term potentiation, and/or to increase acute memory retention, and/or to improve spatial memory performance. Accordingly, in certain methods of the invention, the ligand may be administered in such a way that it crosses the blood-brain barrier. This crossing can result from the physico-chemical properties inherent in the ligand molecule itself, tagging or linking the ligand to a vehicle to facilitate crossing the blood-brain barrier, or from other components in a pharmaceutical formulation, or from the use of a mechanical device such as a needle, cannula or surgical instrument to breach the blood-brain barrier. Where the ligand is a molecule that does not inherently cross the blood-brain barrier, e.g. a fusion to a moiety that facilitates the crossing, suitable routes of administration are, e.g., intrathecal or intracranial. Where the ligand is a molecule that inherently crosses the blood-brain barrier, the route of administration may be by one or more of the various routes described below.

Suitably the ligand or composition comprising same may be administered intracerebrally or more suitably peripherally e.g. by intravenous or subcutaneous injection.

Sterile injectable forms of the compositions described may be aqueous or oleaginous suspension. These suspensions may be formulated according to techniques known in the art using suitable dispersing or wetting agents and suspending agents. The sterile, injectable preparation may be a sterile, injectable solution or suspension in a non-toxic parenterally acceptable diluent or solvent, for example as a suspension in 1,3-butanediol. Among the acceptable vehicles and solvents that may be employed are water, Ringer's solution and isotonic sodium chloride solution, hi addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compositions containing the ligand according to the invention may contain suitable pharmaceutically acceptable carriers. For example, they may contain excipients and/or auxiliaries that facilitate processing of the active compounds into preparations designed for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension include, for example, sodium carboxymethyl cellulose, sorbitol and dextran. Optionally, the suspension may also contain stabilizers. Liposomes also can be used to encapsulate the molecules of the invention for delivery into cells or interstitial spaces. Exemplary pharmaceutically acceptable carriers are physiologically compatible solvents, dispersion media, coatings, antibacterial and antifungal agents, isotonic and absorption delaying agents, water, saline, phosphate buffered saline, dextrose, glycerol, ethanol and the like, in some embodiments, the composition comprises isotonic agents, for example, sugars, polyalcohols such as mannitol, sorbitol, or sodium chloride. In some embodiments, the compositions comprise pharmaceutically acceptable substances such as wetting or minor amounts of auxiliary substances such as wetting or emulsifying agents, preservatives or buffers, which enhance the shelf life or effectiveness of the active ingredients.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in the methods of this invention may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents. Compositions of the invention may be in a variety of forms, including, for example, liquid (e.g., injectable and infusible solutions), dispersions, suspensions, semisolid and solid dosage forms. The preferred form depends on the mode of administration and therapeutic application. For treating tissues in the central nervous system, administration can be, e.g., by injection or infusion into the cerebrospinal fluid (CSF). Administration can also be with one or more agents capable of promoting penetration of a ligand across the blood-brain barrier.

The composition can be formulated as a solution, microemulsion, dispersion, liposome, or other ordered structure suitable to high drug concentration. Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The ligand according to the invention can be formulated with a controlled-release formulation or device. Examples of such formulations and devices include implants, transdermal patches, and microencapsulated delivery systems. Biodegradable, biocompatible polymers can be used, for example, ethylene vinyl acetate, polyanhydrides, polyglycolic acid, collagen, polyorthoesters, and polylactic acid. Methods for the preparation of such formulations and devices are known in the art. See e.g., Sustained and Controlled Release Drug Delivery Systems, J. R. Robinson, ed., Marcel Dekker, Inc., New York, 1978.

Injectable depot formulations can be made by forming microencapsulated matrices of the drug in biodegradable polymers such as polylactide-polyglycolide. Depending on the ratio of drug to polymer, and the nature of the polymer employed, the rate of drug release can be controlled. Other exemplary biodegradable polymers are polyorthoesters and polyanhydrides. Depot injectable formulations also can be prepared by entrapping the drug in liposomes or microemulsions.

Supplementary active compounds can be incorporated into the compositions used in the methods of the invention. These can be therapeutic agents effective to treat, ameliorate or prevent Alzheimer's disease, such as an adrenergic, anti-adrenergic, anti-androgen, anti-anginal, anti-anxiety, anticonvulsant, antidepressant, anti-epileptic, antihyperlipidemic, antihyperlipoproteinemic, a ntihypertensive, antiinflammatory, antiobessional, antiparkinsonian, antipsychotic, adrenocortical steroid; adrenocortical suppressant; aldosterone antagonist; amino acid; anabolic steroid; analeptic; androgen; blood glucose regulator; cardioprotectant; cardiovascular; cholinergic agonist or antagonist; cholinesterase deactivator or inhibitor, such as galantamine, rivastigmine, tacrine and donepezil; cognition adjuvant or enhancer; dopaminergic; enzyme inhibitor, estrogen, free oxygen radical scavenger; GABA agonist; glutamate antagonist; hormone; hypocholesterolemic; hypolipidemic; hypotensive; immunizing; immunostimulant; monoamine oxidase inhibitor, neuroprotective; N-methyl D-aspartate (NMDA) antagonist, such as memantine; AMPA antagonist, competitive or- non-competitive NMDA antagonist; opioid antagonist; potassium channel opener; non-hormonal sterol derivative; post-stroke and post-head trauma treatment; prostaglandin; psychotropic; relaxant; sedative; sedative-hypnotic; selective adenosine antagonist; serotonin antagonist; serotonin inhibitor; selective serotonin uptake inhibitor; serotonin receptor antagonist; sodium and calcium channel blocker; steroid; stimulant; and thyroid hormone and inhibitor agents. The amount of ligand that may be combined with the carrier materials to produce a single dosage form will vary depending upon the host treated, the type of antagonist used and the particular mode of administration. The composition may be administered as a single dose, multiple doses or over an established period of time in an infusion.

Dosage

Dosage regimens also may be adjusted to provide the optimum desired response (e.g., a therapeutic or prophylactic response).

Typically, a physician will determine the actual dosage which will be most suitable for an individual subject. The specific dose level and frequency of to dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

Typically if injected peripherally dosage would be higher, and if injected into the brain dosage would be lower.

Compositions for administration according to the methods of the invention can be formulated so that a dosage of 0.001-10 mg/kg body weight per day of the ligand is administered. In some embodiments of the invention, the dosage may be 0.01-1.0 mg/kg body weight per day. In some embodiments, the dosage may be 0.001-0.5 mg/kg body weight per day.

For treatment with an antibody binding the target $PrP^c$ sequence, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

Doses discussed are for human subjects unless otherwise indicated. Doses for other species are adjusted accordingly. In mice, typical doses are 2 mg/mouse. This is approximately equivalent to a dose of 30 mg/kg. Suitably dosage is 0.1-30 mg/kg.

Most suitably, each protein may be administered at a dose of from 0.01 to 30 mg/kg body weight, preferably from 0.1 to 10 mg/kg, more preferably from 0.1 to 1 mg/kg body weight.

When administering nucleic acid(s) for protein expression, suitably those are administered in amounts capable of supporting levels of expression corresponding to the administration levels mentioned for proteins. Polynucleotides of the invention may be administered directly as naked nucleic acid. When the polynucleotides/vectors are administered as naked nucleic acid, the amount of nucleic acid administered may typically be in the range of from 1 μg to 10 mg, preferably from 100 μg to 1 mg.

The ligand according to the invention may be used as part of a pharmaceutical kit, which may further comprise an administration means. Means for administration include, but are not limited to syringes and needles, catheters, biolistic injectors, particle accelerators, i.e., "gene guns," pneumatic "needleless" injectors, gelfoam sponge depots, other commercially available depot materials, e.g., hydrogels, osmotic pumps, and decanting, polynucleotide coated sutures, skin patches, or topical applications during surgery.

Each of the pharmaceutical kits can further comprise an instruction sheet for administration of the composition to a mammal. If the ligand is provided in lyophilized form, the dried powder or cake may also include any salts, auxiliary to agents, transfection facilitating agents, and additives of the composition in dried form. Such a kit may further comprise a container with an exact amount of sterile pyrogen-free water, for precise reconstitution of the lyophilized components of the composition.

The container in which the composition is packaged prior to use can comprise a hermetically sealed container enclosing an amount of the lyophilized formulation or a solution containing the formulation suitable for a pharmaceutically effective dose thereof, or multiples of an effective dose. The composition is packaged in a sterile container, and the hermetically sealed container is designed to preserve sterility of the pharmaceutical formulation until use. Optionally, the container can be associated with administration means and/or instruction for use.

It has been surprisingly found that prevention of or decrease in PrP:PrP interaction prevents binding of oligomeric A[beta] to PrP. Preferably the ligand that prevents or decreases PrP:PrP interactions prevents PrP oligomerisation from monomers, which as a consequence thereof prevents A[beta] binding. This effect would be complementary to direct inhibition of the ADDL binding site, and/or the target site of PrP described herein. In such a situation, it would therefore be advantageous to administer/use a ligand which inhibits PrP:PrP interaction together with ligand (s) which bind to the PrP target site described herein.

It may also be advantageous to administer/use a ligand which inhibits the ADDL binding region of PrP together with ligand(s) which bind to the PrP target site described herein.

It may also be advantageous to administer a three-way combination of ligands which inhibit PrP:PrP interaction, which inhibit the ADDL binding region of PrP and ligand(s) which bind to the PrP target site described herein.

Ligands that can prevent or decrease PrP:PrP interactions are well-known in the art for treatment of other diseases involving prion proteins, particularly in the central nervous system. Ligands known for their use in preventing or decreasing PrP:PrP interactions, particularly in the central nervous system, are incorporated herein by reference as ligands which may be used in combination with the ligands of the invention.

Ligands which directly target the ADDL binding site of PrP 95-105 are also well known as acknowledged above, and are incorporated herein by reference.

Further Components

The method(s) and application(s) of the invention may further comprise administering an additional therapeutic agent; the invention may relate to compositions such as pharmaceutical compositions comprising a ligand of the invention and an additional therapeutic agent. Additional therapeutic agents include, but are not limited to an adrenergic agent, anti-adrenergic agent, anti-androgen agent, anti-anginal agent, anti-anxiety agent, anticonvulsant agent, anti-depressant agent, anti-epileptic agent, antihyperlipidemic agent, antihyperlipoproteinemic agent, antihypertensive agent, anti-inflammatory agent, antiobessional agent, anti-parkinsonian agent, antipsychotic agent, adrenocortical steroid agent; adrenocortical suppressant agent; aldosterone antagonist agent; amino acid agent; anabolic steroid; analeptic agent; androgen agent; blood glucose regulator; cardioprotectant agent; cardiovascular agent; cholinergic agonist or antagonist; cholinesterase deactivator or inhibitor, such as galantamine, rivastigmine, tacrine and donepezil; cognition adjuvant or enhancer; dopaminergic agent; enzyme inhibitor, estrogen, free oxygen radical scavenger; GABA agonist; glutamate antagonist; hormone; hypocholesterolemic agent; hypolipidemic agent; hypotensive agent; immunizing agent; immunostimulant agent; monoamine oxidase inhibitor, neuroprotective agent; N-methyl D-aspartate (NMDA) antagonist, such as memantine; AMPA antagonist, competitive or-non-competitive NMDA antagonist; opioid antagonist; potassium channel opener; non-hormonal sterol derivative; post-stroke and post-head trauma treatment; prostaglandin; psychotropic agent; relaxant; sedative; sedative-hypnotic agent; selective adenosine antagonist; serotonin antagonist; serotonin inhibitor; selective serotonin uptake inhibitor; serotonin receptor antagonist; sodium and calcium channel blocker; steroid; stimulant; and thyroid hormone and inhibitor agents.

Further Applications

In principle the invention may be applied to any scenario in which it is desired to suppress or interfere with the PrP-Abeta interaction itself. In more detail, the invention may in addition be applied to one or more of inhibiting suppression of long term potentiation, increasing acute memory retention, improving spatial memory performance and/or blocking disruption of synaptic plasticity.

Also described is a ligand which at least part thereof binds to at least part of helix 1 of PrP for use in preventing or improving medical conditions linked to A[beta] oligomerisation. Suitably the A[beta] oligomer is made from soluble non-fibrillar forms of A[beta]. Suitably the A[beta] oligomerisation is A[beta] plaque formation. Suitably the medical condition is synaptic plasticity. Suitably the synaptic plasticity is manifested as Alzheimer's Disease. Suitably the PrP is $PrP^c$. Suitably the ligand is an antibody. Suitably the antibody is humanised.

Advantages

This binding of as 131-153 of the prion protein imparts several advantages over the ligands known in the art which target the ADDL binding region of the prion protein. The ADDL binding region has been linked with toxicity, for example with toxic signalling. Ligands binding this region may contribute to toxic signalling e.g. D13 and IgG P (Solforosi, 2004) or 4H11 (Lefebvre-Roque, 2007). It is an advantage of the invention that such toxicity effects may be avoided.

The ligands according to the present invention selectively recognise the to physiological form of PrP, $PrP^c$, whereas ligands binding the ADDL binding region 95-105 also bind to aberrant forms of the prion protein. Therefore, the ligands according to the present invention may help stabilise the normal form of the protein and in particular do not contribute to stabilising the aberrant form of the protein which may be the case for prior art ligands directed to 95-105.

The ADDL binding region has been suggested to be involved in several possible physiological functions of PrP ranging from metal or glycosaminoglycan binding, endocytosis or preventing oxidative stress. Therefore, blocking said region such as in the art using ligands binding 95-105 may interfere with those physiological functions. It is an advantage of using the ligands described herein that such problems are avoided.

The fact that the ligand which binds to 131-153 is effective in blocking ADDL binding is surprising because the helix 1 region is on the geometrically opposite side of the prion protein from the ADDL binding site region (Zahn, 2000) and therefore would in fact be expected to be one of the least active regions given its structural distance from the ADDL binding region. This is even more surprising in light of recent studies that focus on finding possible ligands for other regions of the prion protein[4,14].

The invention is now described by way of example. These examples are intended to be illustrative, and are not intended to limit the appended claims.

EXAMPLES

Materials. $A[beta]_{1-42}$ was from California Peptide Research Inc. (Napa, Calif.) and biotinylated $A[beta]_{1-42}$ with biotin attached to Asp1 using a 6-carbon linker (bA $[beta]_{1-42}$) was synthesised, and purified by Dr. James I. Elliott at Yale University (New Haven Conn.). Peptide masses and purities were determined by electrospray ionisation/ion trap mass spectrometry and reverse-phase HPLC, respectively. Other reagents were purchased from Sigma Aldrich unless otherwise stated.

Production of ADDL/bADDL Preparations. bA $[beta]_{1-42}$ or $A[beta]_{1-42}$ (~1.25 mg) was weighed into a screw-cap 1.7 ml eppendorf tube, dissolved in ice-cold hexafluoro-2-propanol (HFIP) to a concentration of 1 mM, sonicated for 10 min, the tube sealed and left to stand at room temperature for 1 h. The solution was then transferred to a 2 ml glass vial and the HFIP evaporated under a stream of dry air/$N_2$ to produce a clear film. The peptide film was dissolved in anhydrous DMSO with vigorous vortexing for 10 min to produce a 5 mM solution and then diluted to 100 microM in phenol red-free Ham's F12 medium (Promocell GmbH, Heidelberg, Germany) and vortexed for 15 sec. Equal volumes of sample were then transferred to two separate sealed glass vials and incubated at room temperature for 16 h. Monomeric $A[beta]_{1-42}$ was produced by dissolving $A[beta]_{1-42}$ peptide to 100 microM in 10 mM NaOH (pH 11) for 1 hour and monomeric status was confirmed by size-exclusion chromatography. Finally, samples were centrifuged at 14,200×g for 15 min to remove any large aggregates and the upper 90% for each solution collected, used immediately, or snap frozen in liquid $N_2$ and stored at −80° C.

Size Exclusion Chromatography. 0.5 ml aliquots of freshly prepared 100 microM A[beta]$_{1-42}$ (10 mM NaOH, pH 11), ADDLs and bADDLs (phenol red-free Ham's F12 medium, 2% DMSO) were injected onto a Superdex 75 10/30 column (GE Healthcare) and eluted with PBS at a flow rate of 0.8 ml/min using an AKTA FPLC and peptide elution monitored by absorbance at 280 nm.

Sedimentation Velocity Analytical Ultracentrifugation. Experiments were performed on a Beckman XLI analytical ultracentrifuge. Freshly prepared 100 microM bADDLs (phenol red-free Ham's F12 medium, 2% DMSO) were centrifuged at 50,000 rpm at 20° C. with absorbance data collected at 278 nm. Sedimentation velocity data were analysed as described[32,33] and graphically presented in the standard format with the sedimentation coefficient plotted against the sedimentation coefficient distribution.

Electron Microscopy. For analysis a 4 [micro]l drop of bADDLs/ADDLs was loaded onto negatively glow discharged copper grids which had been previously coated with a continuous carbon film. The sample was left to adhere for 30 sec and excess solution carefully blotted using grade 4 Whatman paper, the sample stained with of 2% uranyl acetate (6 [micro]l) for 30 sec, blotted and the grid left to air dry. Images were recorded on film at a magnification of 42986× using an FEI Tecnai T12 electron microscope operating at 120 kV. Imaging was done at a defocus range of 700 nm to 1 microm and an electron dose of 10-20 electrons per Å$^2$. Films were digitised with a step size of 7 microm using a Zeiss SCAI film scanner, giving a pixel size of 1.63 Å.

SDS-PAGE. Aliquots (5 & 10 [micro]l) of 10 microM bADDL and ADDL preparations were boiled in sample buffer and electrophoresed on 16% polyacrylamide tris-tricine gels and analysed for AR content by comparison to known Aβ standards following visualisation by silver staining. Alternatively, the ADDLs/bADDLS were diluted 1:10 (1 microM) in sample buffer and used without boiling for Western blotting with the N-terminal anti-Aβ antibody, 6E10 (Signet, Dedham, Mass.). Immunoreactive bands were detected and quantified using a Licor Odyssey imaging system (Licor Biosciences, Lincoln, Nebr., USA).

Preparation of human AD brain samples. Three brains were used for this study; one from a 78 year old women with a history of dementia and confirmed Alzheimer's disease pathology (from Asterand, Detroit, Mich.), a second from an 80 year old female (UCL Institute of Neurology brain bank) with clinical and pathological diagnoses of AD and the other from a cognitively intact 68 year old female (UCL Institute of Neurology brain bank). Samples of frozen posterior temporal cortex were thawed on ice and gray matter dissected for use, chopped into small pieces with a razor blade and then homogenised in 5 volumes of ice-cold 20 mM Tris-HCl, pH 7.4, containing 150 mM NaCl (TBS) with 25 strokes of a Dounce homogeniser (Fisher, Ottawa, Canada). To isolate water-soluble Aβ, free from membrane-bound or plaque-associated material, homogenates were centrifuged at 91,000 g and 4° C. in a TLA 55 rotor (Beckman Coultour, Fullerton, Calif.) for 78 min and the supernatant removed and used. In order to eliminate low molecular weight bioactive molecules and drugs, homogenates were dialysed at 4° C. using slide-a-lyzer dialysis cassettes with 2 kDa molecular weight cut-offs (Fisher, Dublin, Republic of Ireland) against a total volume of 5 l of TBS (with 2 changes) over a 48 h period. The dialysate was then aliquoted into 1 ml lots and either stored at −80° C. pending use or used directly to measure the amount and form of Aβ present. For the latter, 0.8 ml of dialysate was immunoprecipitated with AW7[34] at a dilution of 1:80 and analysed by western blotting using a combination of the C-terminal monoclonal antibodies, 2G3 and 21F12 each at a concentration of 2[micro]g/ml (Dr. Peter Seubert, Elan Pharmaceuticals, San Francisco, Calif.). Immunoreactive bands were visualised using a fluorochrome-coupled secondary antibody (Rockland, Gilbertsville, Pa.) and quantified by comparison to synthetic A[beta] standards using a Licor Odyssey imaging system (Licor Biosciences, Lincoln, Nebr., USA).

Generation of FVB/N congenic PrP knockout line. The FVB/N-Prnp $^{o/o}$ (PrP null) congenic line was generated by 10 generations of backcrossing ZH1 PrP null mice[35] to FVB/N followed by genetic testing by Charles River (Margate, UK) using 84 FVB-specific PCR microsatellite makers covering 19 chromosomes at approximately 20 cM intervals to select breeding pairs positive for 100% of the FVB-specific markers. The selected congenic pairs were interbred to remove the endogenous murine PrP gene and to restore homozygosity of the knockout allele.

In vitro electrophysiology. Male, two to four month old FVB/N (Harlan, Wyton, UK) or PrP null mice (MRC Prion Unit) were used to study the effects of bADDLs and A[beta]-containing extracts of human brain. In addition, two to three month old C57BL/6J mice (Charles River, Margate, UK) were used to examine the effects of bADDLs/ADDLs and the anti-PrP antibodies, ICSM-18 and ICSM-35. In all cases, mice were anaesthetised with isoflurane/O$_2$ and decapitated. The brain was rapidly removed and immersed in ice-cold sucrose-based artificial cerebrospinal fluid (sACSF) containing 87 mM NaCl, 2.5 mM KCl, 7 mM MgSO$_4$, 0.5 mM CaCl$_2$, 25 mM NaHCO$_3$, 25 mM Glucose, 1.25 mM NaH$_2$PO$_4$ and 75 mM Sucrose. Parasagital sections (350 microm) were prepared on a Leica VT1000S vibratome using stainless steel razor blades (Campden, Loughborough, UK). Slices were immediately transferred to a holding chamber (BSC-PC, Warner Instruments, Hamden, Conn.) containing ACSF: 119 mM NaCl, 2.5 mM KCl, 1.3 mM MgSO$_4$, 2.5 mM CaCl$_2$, 26.2 mM NaHCO$_3$, 11 mM Glucose and 1.25 mM NaH$_2$PO$_4$. Circulating ACSF was continuously bubbled with a mixture of 95% O$_2$ and 5% CO$_2$ and slices allowed to recover for at least 90 min at room temperature.

Extracellular recordings were performed as described previously (O'Nuallain et al. 2010). Briefly, slices were submerged in a recording chamber and perfused with oxygenated ACSF at a rate of 2-3 ml/min and the perfusate warmed to 30° C. using an inline heating tube (HPT-2A, ALA Scientific Instruments, Westbury, N.Y.). A stainless steel microelectrode (FHC, Bowdoin, USA) was used to stimulate Schaffer collateral fibres, and extracellular field EPSPs (fEPSPs) were recorded from stratum radiatum of CA1 using a glass microelectrode. fEPSPs were recorded using a Multiclamp 700B amplifier in tandem with a Digidata 1440A digitiser (Axon Intruments). Data were collected using pClamp 10 software and analysed using Clampfit 10.2 (Molecular Devices). For all experiments, test stimuli were given once every 30 sec (0.033 Hz), and the stimulus intensity was set to give a baseline fEPSP of 40-50% of the maximal response. A stable baseline was recorded for at least 20 min prior to application of ADDLs/antibody. In experiments using bADDLs/ADDLs (stock solutions were diluted 1:200 into ACSF to produce nominal concentrations of 500 nM based on the starting weight of A[beta]$_{1-42}$ monomer) or TBS extracts of human brain (1 ml of extract diluted into 20 ml ACSF) the sample was added to the perfusate 30 min prior to induction of LTP. Where a combination of ADDLs and anti-PrP antibodies were used, the antibody was added to the perfusate 20 min prior to the ADDLS. LTP was induced by theta burst stimulation (TB, 10 bursts of 4 stimuli at 100 Hz, with an interburst interval of 200 msec) given at baseline intensity. The ACSF was recycled using peristaltic pumps (101 U/R, Watson-Marlow, UK) ensuring that the ADDLs, brain samples and/or antibodies were present for the duration of the experiment. LTP is expressed as the mean±SEM % of baseline fEPSP slope. Statistical comparisons used ANOVA with post hoc Tukey-Kramer test. All experiments were interleaved with respect to genotype. In addition, vehicle and ADDL/bADDL/human brain derived A[beta] experiments were performed on the same day ensuring each animal was its own control while alternating treatments daily to avoid any temporal bias.

In vivo electrophysiology. In vivo studies on urethane (1.5 gm/kg i.p.) anaesthetised male Adult Wistar rats (250-300 g) were approved by Trinity College Dublin's ethical review committee and by the Department of Health, Republic of Ireland. Electrodes were made and implanted as described previously[36]. Briefly, twisted-wire bipolar electrodes were constructed from Teflon-coated tungsten wires (62.5[micro]m inner core diameter, 75[micro]m external diameter). Single pathway recordings of fEPSPs were made from the stratum radiatum in the CA1 area of the right hippocampal hemisphere in response to stimulation of the ipsilateral Schaffer collateral—commissural pathway. Electrode implantation sites were identified using stereotaxic coordinates relative to bregma, with the recording site located 3.4 mm posterior to bregma and 2.5 mm right of midline, and the stimulating electrode located 4.2 mm posterior to bregma and 3.8 right of midline. The optimal depth of the wire electrodes in the stratum radiatum of the CA1 region of the dorsal hippocampus was determined using electrophysiological criteria and verified post-mortem. Test fEPSPs were evoked at a frequency of 0.033 Hz and at a stimulation intensity adjusted to elicit a fEPSP amplitude of 50% of maximum. The high frequency stimulation (HFS) protocol for inducing LTP consisted of 10 bursts of 20 stimuli with an inter-stimulus interval of 5 msec (200 Hz), and an inter-burst interval of 2 sec. The intensity was increased to give an EPSP of 75% of maximum amplitude during the HFS. To inject samples, a stainless-steel guide cannula (22 gauge, 0.7 mm outer diameter, 13 mm length) was implanted above the right lateral ventricle (1 mm lateral to the midline and 4 mm below the surface of the dura) just prior to electrode implantation. Animals received two intracerebroventricular (i.c.v.) injections via an internal cannula (28 gauge, 0.36 mm outer diameter). The first injection contained water vehicle, ICSM-18 or mouse IgG1 isotype control antibody (MAB002, R&D Systems, Minneapolis) in a 10 [micro]l volume. The second injection (5[micro]l), which contained either water vehicle or human brain TBS extract, was administered 30 min later, 15 min before the HFS. The experimenter was blinded regarding treatment group in the experiment directly comparing ICSM-18 and control antibody. Verification of the placement of the cannula was performed post-mortem by checking the spread of i.c.v. injected ink dye. LTP is expressed as the mean±SEM % baseline field EPSP amplitude recorded over at least a 30 minute baseline period. Similar results were obtained when the EPSP slope was measured. Statistical comparisons used ANOVA with post hoc Tukey test, paired and unpaired Student t-tests or Mann Whitney U-test, as appropriate.

Protein Expression and Purification. Constructs of human PrP were expressed[37] and purified[38] as described previously. Protein quality was confirmed by SDS-PAGE, MALI-TOF mass spectrometry and Circular Dichroism spectroscopy.

DELFIA® assay[39]. 100[micro]l of 1 [micro]M human PrP (10 mM sodium carbonate, pH 9.6) was bound to medium binding 96-well white plates (Greiner) overnight at 4° C., washed with 3×300 [micro]l of PBS (0.05% Tween-20), blocked with 300 [micro]l 2% BSA in PBS (0.05% Tween-20) at 37° C. for 2 h and washed with 3×300 [micro]l of PBS (0.05% Tween-20). If required, 100 [micro]l of antibody was then incubated in PBS (0.05% Tween-20) for 1 hour and washed with 3×300 [micro]l of PBS (0.05% Tween-20). 100 [micro]l of different preparations of A[beta]$_{1-42}$ were incubated in PBS (0.05% Tween-20, 0.1% BSA) for 1 hour and washed with 3×300 [micro]l of PBS (0.1% Tween-20). A[beta] was detected by 100 [micro]l of 1 [micro]g/ml 6E10 in PBS (0.05% Tween-20) for 1 hour, washed with 3×300 [micro]l of PBS (0.05% Tween-20), to incubated for 30 min with 300 ng/ml of DELFIA® Eu-N1 anti-mouse antibody in DELFIA® assay buffer, washed with 3×300 [micro]l of PBS (0.05% Tween-20) before enhancing with 100 [micro]l of DELFIA® Enhancement Solution. Biotinylated A[beta] was detected by 100 [micro]l of 50 pM DELFIA® Eu-N1 Streptavidin (DELFIA® assay buffer) and washed with 3×300 [micro]l of PBS (0.05% Tween-20) before enhancing with 100 [micro]l of DELFIA® Enhancement Solution.

Antibody Binding (Affinity) Determination

For PrP antibody-binding experiments (e.g. determining the affinity of ligands for PrP) ICSM antibodies were incubated for 30 min with 300 ng/ml of DELFIA® Eu-N1 anti-mouse antibody in DELFIA® assay buffer, washed with 3×300 [micro]l of PBS (0.05% Tween-20) before enhancing with 100 [micro]l of DELFIA® Enhancement Solution. Binding of antibodies to PrP was detected by incubated for 30 min with 300 ng/ml of DELFIA® Eu-N1 anti-mouse antibody in DELFIA® assay buffer, washed with 3×300 [micro]l of PBS (0.05% Tween-20) before enhancing with 100 [micro]l of DELFIA® Enhancement Solution. Plates were scanned for time-resolved fluorescence intensity of the europium probe ($\lambda_{ex}$=320 nm, $\lambda_{em}$=615 nm) using a Perkin Elmer EnVision plate reader. Binding Constants were calculated using a 1-site Langmuir isotherm and were tested for tight binding characteristics using the equation $y=(F_{min}+(((L+E_o+K_d)-(((L+E_o+K_d)^2)-4*E_o*L)^{0.5})/(2*E_o))*(F_{max}-F_{min}))$ where $F_{min}$=minimum fluorescence, $F_{max}$=maximum fluorescence, $E_o$=the total concentration of binding sites, $K_d$=the dissociation constant and L=total A[beta] concentration. This ensures a true $K_d$ can be measured and that direct saturation of the protein surface as soon as stoichiometric quantities of peptide are added has not occurred.

Molecular modelling. A model of the full ISCM-18 antibody complex with human $PrP^c{}_{119-231}$ was constructed as follows. Two copies of the corresponding PrP-Fab complex (2W9E) were superimposed onto on the Fab domains of a full human IgG antibody structure (1 HZH). The human Fab domains were removed and the loops between the 1 HZH-Fc and 2W9E-Fab domains rebuilt.

Example 1—The ADDL particle was constructed by first building a full atomic model of $A\beta_{1-42}$ as an extended β strand with uncharged side-chains and termini. This molecule was subjected to molecular dynamics simulation at 1000K for 0.1 nsec and structures saved every 1 psec. The chain collapsed into a globular structure after 25 psec of simulation and the 57 most compact structures were chosen from the last 75 psec of the simulation. The maximum spatial extent of these selected molecules was measured (in all three dimensions) and found to be just below 3.0 nm. These 57 molecules were placed at random in the 57 vacant sites of spherical array made by removing the appropriate 8×8.5 corner sites (i.e. 7 per corner and 3 shared with adjacent corners) of a 5×5×5 cubic array with a 3.0 nm lattice spacing. The protonation state of the 57 $A\beta_{1-42}$ molecules was reset to correspond to pH 7, water molecules were added in a 3.5 Å layer around each polypeptide and the complex relaxed 2000 steps of energy minimisation. The complex was subjected to 0.1 nsec of molecular dynamics at 300K resulting in a roughly spherical, hydrated ADDL model with a diameter around 10 nm (and a corresponding protein density of 0.82 $gl^{-1}$).

The N-terminus of the $PrP^c$ molecule, taken from the Fab crystal structure complex (2W9E), was extended back to residue 95 as an unstructured polypeptide. Copies of this molecule were manually docked to the surface of the ADDL particle in an annulus around the "equator" to illustrate how lateral interactions between such surface-bound prion molecules might occlude helix 1 and so compromise ISCM-18 binding. Molecular graphics and model building was performed using InsightII (2005) and energy calculations using Discover 2.98 (Accelrys).

Example 1

Characterisation of Reproducible Preparations of ADDLs

A standardised procedure to generate ADDL preparations from $A[beta]_{1-42}$ or bADDL preparations from biotinylated $A[beta]_{1-42}$ ($bA[beta]_{1-42}$) was used and then assessed the consistency of the species produced using a battery of biophysical tests. Both normal and biotinylated A[beta] were used to confirm that biotinylation did not fundamentally alter the properties of the oligomers.

Size-exclusion chromatography (SEC) using 3 different running buffers showed that both ADDLs and bADDLs had highly similar profiles producing two prominent peaks (FIG. 1*a* and FIG. 2). The first peak eluted in the void volume and the second eluted in a volume consistent for Aβ monomer[21]. Moreover, both peaks had trailing and leading shoulders suggesting the presence of low abundance oligomers intermediate in size between Aβ monomer and the void material. Given the limited size resolution of SEC, and the possibility of forming artefacts owing to non-ideal interactions with the column, the bADDL preparations were also analysed using a solution-based technique, analytical ultracentrifugation (FIG. 1*b*). Sedimentation of bADDLs occurred in two distinct phases containing approximately 60 and 40% of the material, respectively. The initial sedimentation contained a mixture of species with calculated masses ranging from 90-400,000 and accounted for around 60% of the peptide. The slowly sedimenting portion contained a single species with calculated molecular weight of 5-6,000 close to the value expected for monomeric, biotinylated A[beta] peptide. In agreement with the SEC results, the AUC data confirm that bADDL preparations are heterogeneous and include Aβ monomer, small amounts of low n-oligomers and species with calculated masses >90,000. It is noteworthy that in all samples tested bADDL preparations contained slightly greater amounts of high molecular weight species than did ADDLs (FIGS. 1*a* & 2). Consistent with other biophysical assessments, negative-stain electron microscopy confirmed that ADDL and bADDL preparations contained a mixture of different sized species, ranging from globular structures of 8-12 nm diameter and flexible rods of 15-60 nm in length and 5-10 nm diameter (FIG. 1*c* and FIG. 3). These structures are reminiscent of those detected by Laurén et al.[1], but are in contrast to the entirely globular structures observed by Chen et al.[14] when prepared using simple phosphate buffer. The species detected by SEC, AUC and EM were SDS-labile and migrated on SDS-PAGE predominantly as monomer (FIG. 1*d*), however a small amount of higher molecular weight Aβ species were detected if samples were not boiled prior to SDS-PAGE and proteins visualised by Western blotting. Since a major factor which has been found to influence production of ADDL preparations of consistent composition is the effective solubilisation of HFIP-treated Aβ, SDS-PAGE and silver staining as a simple means to measure the total amount of Aβ present in all the ADDL preparations was used. These experiments revealed that the actual concentration of total Aβ in the ADDL preparations varied between 70 to 90 microM (based on the molecular weight of Aβ monomer), less than the 100 microM concentration based on the starting amount of Aβ used.

Example 2

Both AD Brain-derived A[beta] and ADDLs Inhibit LTP in a PrP-Dependent Manner Having established procedures to produce and characterise the bADDL and ADDL preparations, their effect on synaptic plasticity and to determine if this effect required expression of PrP was assessed. As expected, both the bADDL and ADDL preparations significantly inhibited LTP in hippocampal slices from wild type FVB/N and C57B6/J mice ($P<0.01$, FIG. 4*a* and FIG. 5). Using an FVB/N congenic PrP-null mouse line was next investigated if this Aβ-mediated inhibition of LTP required, the expression of PrP. As in a prior study using another PrP null mouse models, bADDLs that blocked LTP in wild type mice failed to impair LTP in the hippocampi of the PrP null mice (FIG. 4*b*). While these results suggest a potential role for PrP in bADDL-mediated depression of hippocampal LTP it is not clear if such preparations include Aβ species that occur in AD brain. Therefore, the fact if water-soluble extracts of AD brain that contain SDS-stable Aβ dimers also required the expression of PrP for their plasticity impairing effects was determined. For these experiments a brain extract from a non-demented control subject that lacked detectable Aβ and a tris-buffered saline (TBS) extract from an AD brain that contained significant amounts of Aβ monomer and SDS-stable dimer (FIG. 4*c*) were used. As in earlier experiments[22] the Aβ-containing extracts potently inhibited LTP in slices from FVB/N mice (FIG. 4*d*, $P>0.05$), whereas TBS extracts that lacked Aβ had no effect (FIG. 4*d*). Importantly, as was the case with bADDLs (FIG. 4*b*), the block of LTP mediated by brain-derived Aβ required the expression of $PrP^c$, with the AD-TBS extract unable to alter LTP in hippocampal slices from PrP null mice (FIG. 4*d*). As expected, application of TBS from a control brain, that lacked detectable amounts of Aβ, had no effect on LTP in slices from either PrP expressing or PrP null FVB/N mice (FIGS. 4*d* and 168±10% vs 164±10%, respectively). These findings provide important evidence that PrP is required for the plasticity impairing effects of pathogenically relevant brain-derived Aβ species and suggest that PrP may be required for the changes in synaptic function that characterise the earliest stages of AD[23]. With regard to how the active A[beta] species in human brain relate to the active species present in an Aβ preparation such as ADDLs, it is worth pointing out that both sources are heterogenous. In the case of aqueous extracts of human brain, SDS-stable dimers have been shown to mediate synaptotoxicity, however, these need not necessarily exist as discrete Aβ dimers, but could also include larger assemblies built from SDS-stable dimers[22,24] some of which may overlap in size and structure with assemblies present in the highly heterogenous ADDL preparation (FIG. 1 and Hepler et al[20]).

Example 3

High Affinity PrP:ADDL Interaction can be Targeted at Multiple Sites

Having established the requirement for PrP for the plasticity impairing activity of both AD brain-derived Aβ and ADDLs, the binding of active preparations of Aβ to PrP was investigated. Previous characterisation of the PrP:A[beta] interaction has been carried out using preparations of synthetic Aβ that acted in a PrP-independent manner[3], had not been shown to be toxic[4,14] or were studied at micromolar concentrations[3,14]. The interaction using a high-throughput plate-based DELFIA® assay was probed. A binding response between huPrP$_{23-231}$ and either bADDLs or ADDLs was detected at low nanomolar concentrations with apparent dissociation constants for total A[beta] of 82±7 nM and 100±30 nM, respectively (FIG. 6a), with no indication of a tight-binding component (see materials and methods). Given that the total concentration of Aβ present in the stock solution was on average 20% less than the 100 microM value derived from the weight of starting peptide powder, that a significant portion of the peptide remained as monomer (FIG. 1a and b), and that the molar concentration of Aβ oligomers must (because of their higher molecular weight) be lower than the concentration based on monomer content, it is evident that one or more of the species present in ADDL preparations binds PrP very tightly, probably in the picomolar range. In contrast, Aβ monomer exhibited no binding to PrP at concentration≤3×10$^{-7}$M (FIG. 13a). Non-specific oligomer binding to a background BSA surface was observed for both ADDLs and bADDLs when the concentration was raised from high nanomolar to low micromolar, highlighting the importance of probing this interaction in the nanomolar range using well defined oligomer preparations. Moreover, the modest binding observed when micromolar concentrations of monomer were used likely resulted because spontaneous aggregation of Aβ occurs in this concentration range[24] and once formed such aggregates could bind to PrP. Consequently, all subsequent experiments were carried out using bADDLs at a concentration of 100 nM (monomer equivalent A[beta]) where the most specific interaction could be measured. Given that both PrP[25] and A[beta][26] are known to contain high affinity copper binding sites in relevant positions, the possibility that their interaction may be mediated by copper chelation was investigated. Addition of up to 10 mM EDTA did not change the level of bADDL binding (FIG. 7). At these concentrations EDTA should be capable of displacing copper from both PrP and A[beta][27] thus excluding simple, non-specific copper chelation as the mechanism for the PrP:A[beta] interaction.

The binding to different length constructs of PrP showed that huPrP$_{91-231}$ bound similar quantities of bADDLs as did the full length construct, suggesting the crucial high affinity binding site was not in the region 23-91 (FIG. 6b). In contrast, huPrP$_{119-231}$ displayed almost no binding, confirming the role of the 91-119 region in the high affinity PrP:A[beta] interaction. A competition assay, whereby increasing concentrations of the different PrP constructs were co-incubated with bADDLs to prevent binding to surface-bound huPrP$_{23-231}$, confirmed that the interaction could occur in solution and revealed that whilst the region 23-90 did not appear to contain a separate high-affinity binding site, it was indeed involved in modulating the high affinity interaction (FIG. 6c). The ability of the antibody ICSM-35, which binds to an epitope contained in residues 95-105 of PrP[7], the putative site of ADDL binding[1] was then tested for its ability to block the PrP:Aβ interaction. This antibody blocked binding of bADDLs to PrP in a classical dose-dependent manner with an IC$_{50}$=10.4±1.7 nM (FIG. 6d). A screen of 28 PrP-binding antibodies pre-incubated with PrP prior to the addition of bADDLs showed that all antibodies that bound fully to PrP were capable of blocking bADDL binding, at least in vitro, although their efficacy varied (FIG. 6e). The differences in efficacy were clearly epitope dependent, with those interacting directly with the putative ADDL binding site most effective, followed by those that bind to helix 1 of PrP, while those binding to other structured regions of the protein were the least effective. There was no epitope-dependent correlation between the level of antibody binding and the level of inhibition although, as expected, individual antibodies that failed to remain bound to PrP did not inhibit bADDL binding. Furthermore, the two best characterised antibodies that bind to helix 1 and the 95-105 epitope (ICSM-18 and ICSM-35, respectively), both bind to full-length human prion protein with affinities of approximately 10 nM, block A[beta] oligomer with inhibition constants of approximately 20 nM, yet still differ in the magnitude of their inhibition (FIG. 13) ICSM-18 and ICSM-35 were chosen for further characterisation as representative members of the groups that bind to helix 1 and the 95-105 epitope respectively, due to their proven efficacy as anti-prion therapeutics without causing acute toxicity[6] and because the structure of the PrP:ICSM-18 complex has been solved at atomic resolution[8].

The ability of ICSM-18 to block the interaction, despite binding to an epitope far-removed from the 95-105 segment, is surprising (FIG. 6f). It is unlikely that the on-rate of PrP with the A[beta] is reduced significantly by linking with the antibody, since the enlarged structure will diffuse only slightly more slowly. The dissociation rate of PrP from the A[beta] structure is not likely to increase by linking interactions with the antibody owing to bulk-solvent effects. The antibody is also unlikely to cause disruption of the water structure or dielectric properties around the PrP:A[beta] interface; hence, hydrophobic or electrostatic interactions will be largely unaffected. However, if PrP:PrP contact is needed to stabilize the PrP layer adhered to the A[beta] aggregates, then interaction with the antibody would certainly prevent this and weaken the system. Multiple PrP binding sites would suggest the oligomer contains a repeat structure. It may be that such antibodies prevent the binding of larger Aβ assemblies but not smaller species. Likewise, reorganisation of the protein on the membrane surface could bring these epitopes into close proximity allowing ICSM-18 to sterically block the interaction, although this is unlikely to be the cause of the effect in a plate-based biochemical assay and would not explain the stronger inhibition of helix 1 directed antibodies compared to those that bind to structured areas closer to the A[beta] oligomer binding site. Either option opens up the possibility of using multiple antibodies to therapeutically block this interaction. Moreover, these results validate the use of this novel high throughput system as a useful first round screen to identify candidate therapeutics capable of inhibiting or modulating ADDL binding to PrP.

Example 4

Therapeutic Antibodies Block the Aβ-mediated Disruption of LTP In Vivo

Figure 4A:
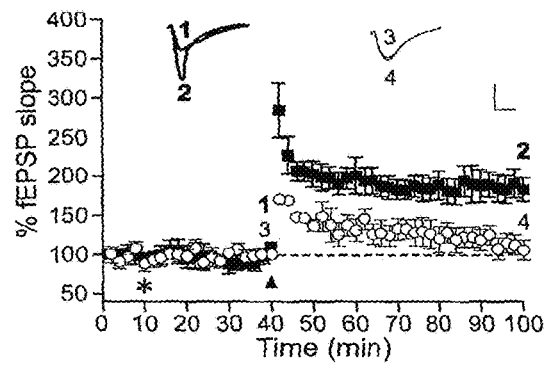
FIGS. 4A-4D: $PrP^c$ is required for the inhibition of LTP by bADDLs and A[beta]-containing extracts of human brain fEPSPs were recorded from the CA1 region of the hippocampus in all cases. Insets show example fEPSP traces before and 1 h. post theta-burst stimulation (TB, stimulus artefact was removed for clarity).
Figure 4B:
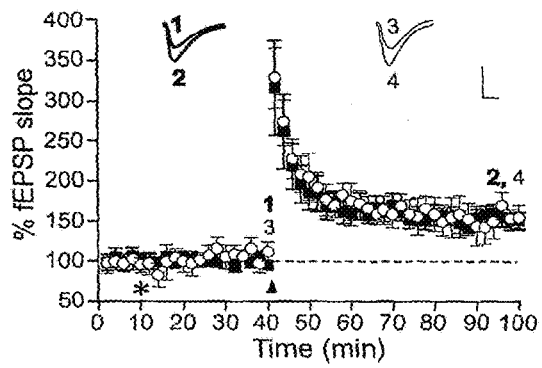
Figure 4C:
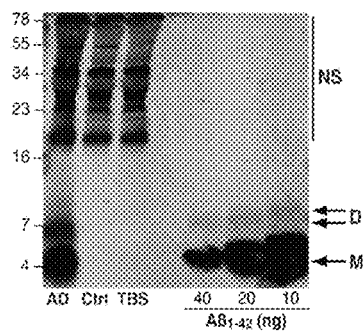
Figure 4D:
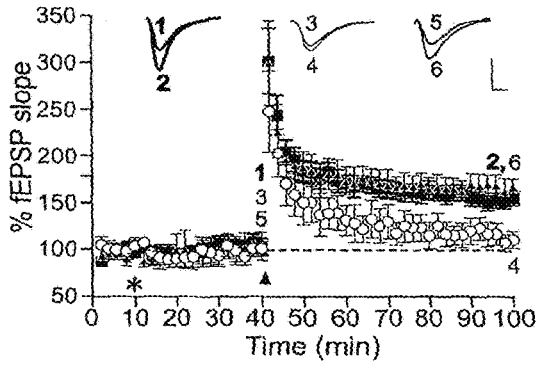
Figure 5:
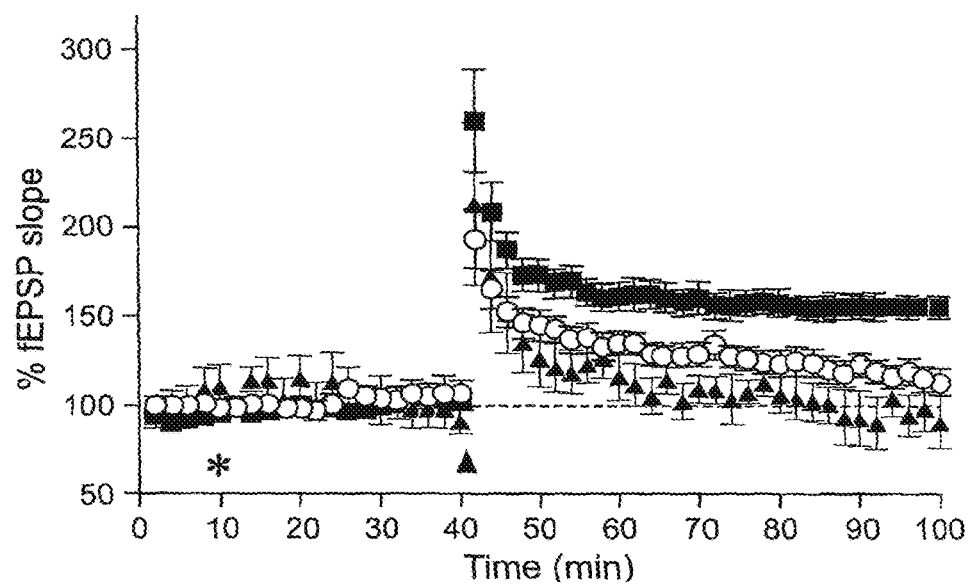
FIG. 5: ADDLs and bADDLS potently inhibit hippocampal LTP

To further assess the potential of two lead monoclonal antibodies identified in our screen, and that belong to the two groups of antibodies that most effectively blocked ADDL binding to PrP in vitro (FIG. 6e), it was examined if these antibodies could also block Aβ-mediated impairment of synaptic plasticity. To ensure the effect was not just present it FVB/N mice, this part of the study was carried out using in the C57B6/J model, more commonly used for electrophysiological studies. Perfusion of hippocampal slices from C57B6/J to mice with ADDLs 30 min prior to LTP induction significantly depressed LTP compared to slices treated with buffer control alone (FIG. 9a, p<0.01), whereas prior application of low concentrations of the anti-PrP antibody, ICSM-35 (2 [micro]g/ml, 13 nM) abolished the ADDL-mediated impairment of LTP (FIG. 9a, p<0.01). Similarly, when slices were incubated with ICSM-18 20 min prior to ADDLs this antibody also protected against the ADDL-mediated block of LTP (FIG. 9b, p<0.01). Importantly both ICSM18 and ICSM35 had no significant effect on LTP when administered alone (FIG. 8a & b). ICSM-35 is directed against amino acids 93-102 of $PrP^c$ which includes the Aβ:PrP binding domain identified in this and prior studies[1], whereas, ICSM-18, selectively binds to helix 1 of $PrP^8$. Thus unlike ICSM-35, which should directly target the ADDL binding site, ICSM-18 may act by hindering formation of the PrP:A[beta] interaction. Having found that anti-PrP antibodies prevented ADDL-mediated inhibition of LTP in mouse hippocampal slices, next it was examined the in vivo efficacy of one of the antibodies, ICSM-18, in a different species, the rat. This would confirm if the PrP-dependence of A[beta] oligomer toxicity was species as well as mouse strain independent. A comparison of the ability of ICSM-18 with an IgG1 isotype control antibody to abrogate the inhibition of hippocampal LTP by the pathophysiologically relevant Aβ-containing TBS extract of AD brain was made. In addition, to confirm that the involvement of PrP was generalisable extracts from different AD and control brains than those used in FIG. 4d were used. Intracerebroventricular (i.c.v.) pre-injection of the anti-PrP antibody completely prevented the AD brain Aβ-mediated inhibition of high frequency stimulation (HFS)-induced LTP. In contrast, animals injected with AD brain extract immunodepleted of Aβ (FIG. 10) no longer blocked LTP (131±6, n=6; p<0.05 compared with baseline; p>0.05 compared with vehicle injected controls at 3 h). Thus, acute administration of soluble extract from AD brain (5 [micro]l, i.c.v.) (FIGS. 9c and 10) completely inhibited LTP at 3 h post-HFS in an Aβ-dependent manner in animals injected 30 min previously with the control antibody (30 [micro]g in 10 [micro]l, i.c.v.) (p>0.05 compared with baseline; p<0.05 compared with controls that received two vehicle injections). In contrast, in animals that were pre-injected i.c.v. with ICSM-18 (30 [micro]g) HFS induced robust LTP (p<0.05 compared with baseline and compared with AD brain Aβ+ control IgG1) that was similar in magnitude to controls (p>0.05). When injected alone, neither ICSM 18 nor the control IgG1 significantly affected the magnitude of LTP (FIG. 8c). The finding that sequence-selective targeting of PrP using antibodies can ameliorate the plasticity impairing activity of AD brain-derived material in rats in vivo corroborates the in vitro finding with ADDLs and strongly supports further exploration of this approach as an attractive therapeutic strategy.

To highlight the importance of the helix-1 epitope as a possible therapeutic target for abeta toxicity independently of the antibody scaffold we tested the ability of a humanised (IgG4) form of ICSM18 (PRN100) to block AD brain Abeta-mediated inhibition of high frequency stimulation (HFS)-induced LTP. Results are shown in FIG. 14. PRN100 completely blocked the inhibition of LTP (grey triangles) seen when AD brain was injected alone (red circle) or in the presence of a control human IgG4 (pink triangles), compared to vehicle control (black squares). This confirms that ligands such as engineered antibodies that bind to helix-1 could be used to target PrP in the brain and block toxic effects linked to human Alzheimer's disease. That this has been successfully achieved with a fully humanised antibody further demonstrates their therapeutic potential.

Conclusions from the Examples

These data support the earlier finding that $PrP^c$ acts as a receptor for mediating toxicity of certain Aβ species. That the inhibitory effect of ADDLs on synaptic plasticity is $PrP^c$-dependent has been confirmed using in vitro LTP recordings from congenic wild type and PrP null mice and importantly that PrP expression is required for the plasticity-impairing activity of human brain-derived Aβ. There has been much debate about the nature of biologically relevant A[beta] oligomers. Here two distinct preparations were used, one prepared from synthetic $Aβ_{1-42}$ to form ADDLs, and which were confirmed to be biologically active and the other derived from the water-soluble phase of human AD brain. By using ADDLs which are known to be active and to have similar biophysical characteristics as those used by Lauren et. al the veracity of earlier reports that Aβ toxicity was mediated (at least in part) through PrP could be tested. Importantly, both preparations inhibited LTP in a PrP-dependent manner, suggesting that the ADDL preparation contained a component with similar properties to those found in AD brain. Heterogeneous preparations of Aβ aggregates are known to have non-specific cytotoxicity at high concentrations and it would therefore be incorrect to interpret a failure of PrP targeting to ameliorate such non-specific toxicity as excluding a role for PrP in Aβ mediated neurotoxicity. AD is a clinicopathological syndrome not a single disease, with multiple aetiologies. To expect PrP ablation to block toxicity in all aspects of all models would be to oversimplify a complex problem. The dependence of toxicity on particular receptors in individual animal models of AD may allow us to ascertain which models correctly mimic particular aspects of AD.

A number of synaptic proteins have been shown to affect the binding and toxic effects of A[beta]. mGluR5 was shown to affect binding of Aβ oligomers to excitary synapses with anti-mGluR5 receptors antibodies reducing A[beta] oligomer binding by 50%[28]. This is a similar level of reduction shown by PrP[1]. Whilst the effect of this receptor on A[beta] binding was directly visualised, a binary interaction between A[beta] and mGluR5 has not been proven. EphB2 was recently shown to co-precipitate with cell derived oligomers and fibronectin repeat domain was shown to be critical[29]. Again, a direct binary interaction has not been proven. The LTP deficit in the J20 mouse model of AD, caused by down-regulation of NMDAR, was reversed by over expressing EphB2 and it would be interesting to see if this also applies to exogenous human brain-derived A[beta] oligomers or whether this requires in situ A[beta] present over longer periods. Previous studies have shown NMDAR are involved in toxic effects related to ADDLs but appear not to bind directly[30]. Given that PrP has been suggested to interact with NR2D subunits and attenuate excitotoxicity[31] it is plausible that a number of these proteins are involved in A[beta] toxicity through similar pathways. In that sense, the lack of a vital PrP function would make it a most attractive therapeutic target.

In addition, the demonstration that A[beta]-mediated inhibition of LTP in vivo and in vitro can be blocked by anti-PrP antibodies further extends these findings, arguing against the effect in PrP null mice being due to unknown protective effects of constitutive PrP ablation. That antibodies raised against two structurally and sequentially different regions of the protein are active strongly argues that PrP is the target of these antibodies in vivo and that the effect is not non-specific. Furthermore, these same antibodies have already been used to successfully treat prion disease in mice without causing toxic effects[6]. The PrP:Aβ binding interaction has been further characterised using material of known biological activity and a biophysical assay developed to investigate potential therapeutic agents which might efficiently disrupt this interaction. The anti-PrP monoclonal antibodies ICSM-18 and 35, already extensively studied in vivo in mouse and fully humanised for investigation as putative human anti-prion therapeutics, potently inhibit Aβ-induced effects on synaptic plasticity both in vitro and in vivo suggesting that these and/or humanised versions of these antibodies find application as AD therapeutics either individually or in combination. Since both ADDL preparations and Aβ extracted from human brain in aqueous buffer are highly heterogeneous, additional studies may help to biophysically characterise the key toxic species that bind to PrP.

REFERENCE LIST

1. Lauren, J., Gimbel, D. A., Nygaard, H. B., Gilbert, J. W., & Strittmatter, S. M. Cellular prion protein mediates impairment of synaptic plasticity by amyloid-beta oligomers. *Nature* 457, 1128-1132 (2009).
2. Gimbel, D. A. et al. Memory impairment in transgenic Alzheimer mice requires cellular prion protein. *J. Neurosci.* 30, 6367-6374 (2010).
3. Balducci, C. et al. Synthetic amyloid-beta oligomers impair long-term memory independently of cellular prion protein. *Proc. Natl Acad. Sci. USA* 107, 2295-2300 (2010).
4. Calella, A. M. et al. Prion protein and abeta-related synaptic toxicity impairment. *EMBO Mol Med* (2010) 2, 306-314.
5. Kessels, H. W., Nguyen, L. N., Nabavi, S. & Malinow, R. The prion protein as a receptor for amyloid-beta. *Nature* 466, E3-E4 (2010).
6. White, A. R. et al. Monoclonal antibodies inhibit prion replication and delay the development of prion disease. *Nature* 422, 80-83 (2003).
7. Khalili-Shirazi, A. et al. Beta-PrP form of human prion protein stimulates production of monoclonal antibodies to epitope 91-110 that recognise native PrP(Sc). *Biochim. Biophys. Acta* 1774, 1438-1450 (2007).
8. Antonyuk, S. V. et al. Crystal structure of human prion protein bound to a therapeutic antibody. *Proc. Natl Acad. Sci. USA* 106, 2554-2558 (2009).
9. Walsh, D. M. & Selkoe, D. J. A beta oligomers—a decade of discovery. *J. Neurochem.* 101, 1172-1184 (2007).
10. Cullen, W. K., Suh, Y. H., Anwyl, R. & Rowan, M. J. Block of LTP in rat hippocampus in vivo by beta-amyloid precursor protein fragments. *Neuroreport* 8, 3213-3217 (1997).
11. Lambert, M. P. et al. Diffusible, nonfibrillar ligands derived from Abeta1-42 are potent central nervous system neurotoxins. *Proc. Natl Acad. Sci. USA* 95, 6448-6453 (1998).
12. Wang, H. W. et al. Soluble oligomers of beta amyloid (1-42) inhibit long-term potentiation but not long-term depression in rat dentate gyrus. *Brain Res.* 924, 133-140 (2002).
13. Klyubin, I. et al. Soluble Arctic amyloid beta protein inhibits hippocampal long-term potentiation in vivo. *Eur. J. Neurosci.* 19, 2839-2846 (2004).
14. Chen, S. G., Yadav, S. P. & Surewicz, W. K. Interaction between human prion protein and amyloid-beta (A beta) oligomers ROLE OF N-TERMINAL RESIDUES. *J. Biol. Chem.* 285, 26377-26383 (2010).
15. Chung, E. et al. Anti-PrP$^c$ monoclonal antibody infusion as a novel treatment for cognitive deficits in an Alzheimer's disease model mouse. *BMC Neuroscience* 11, (2010).
16. Nicoll, A. J. & Collinge, J. Preventing prion pathogenicity by targeting the cellular prion protein. *Infect. Disord. Drug Targets* 9, 48-57 (2009).
17. Mallucci, G. et al. Post-natal knockout of prion protein alters hippocampal CA1 properties, but does not result in neurodegeneration. *EMBO J.* 21, 202-210 (2002).
18. Mallucci G. et al. Depleting neuronal PrP in prion infection prevents disease and reverses spongiosis. *Science* 302, 871-874 (2003).
19. Nicoll, A. J. et al. Pharmacological chaperone for the structured domain of human prion protein. *Proc. Natl. Acad. Sci. USA* 107, 17610-17615 (2010).
20. Hepler, R. W. et al. Solution state characterization of amyloid beta-derived diffusible ligands. *Biochemistry* 45, 15157-15167 (2006).
21. Walsh, D. M., Lomakin, A., Benedek, G. B., Condron, M. M. & Teplow, D. B. Amyloid beta-protein fibrillogenesis—Detection of a protofibrillar intermediate. *J. Biol. Chem.* 272, 22364-22372 (1997).
22. Shankar, G. M. et al. Amyloid-beta protein dimers isolated directly from Alzheimer's brains impair synaptic plasticity and memory. *Nat. Med.* 14, 837-842 (2008).
23. Shankar, G. M. & Walsh, D. M. Alzheimer's disease: synaptic dysfunction and Abeta. *Mol Neurodegener.* 4, 48 (2009).
24. O'Nuallain, B. et al. Amyloid-beta protein dimers rapidly form stable synaptotoxic protofibrils. *J. Neurosci.* 30, 14411-14419 (2010).
25. Jackson, G. S. et al. Location and properties of metal-binding sites on the human prion protein. *Proc. Natl. Acad. Sci. USA* 98, 8531-8535 (2001).
26. Atwood, C. S. et al. Characterization of copper interactions with Alzheimer amyloid beta peptides: Identification of an attomolar-affinity copper binding site on amyloid beta 1-42. *J. Neurochem.* 75, 1219-1233 (2000).
27. Data for biochemical research. Dawson, R. M. C., Elliot, D., Elliot, W. & Jones, K. M. (eds.), pp. 399-415 (Clarendon Press, Oxford,1986).
28. Renner, M. et al. Deleterious Effects of Amyloid beta Oligomers Acting as an Extracellular Scaffold for mGluR5. *Neuron* 66, 739-754 (2010).
29. Cisse, M. et al. Reversing EphB2 depletion rescues cognitive functions in Alzheimer model. *Nature* 469, 47-52 (2011).

30. Decker, H. et al. N-Methyl-d-aspartate receptors are required for synaptic targeting of Alzheimer's toxic amyloid-beta peptide oligomers. *J. Neurochem.* 115, 1520-1529 (2010).
31. Khosravani, H. et al. Prion protein attenuates excitotoxicity by inhibiting NMDA receptors. *J Cell Biol.* 181, 551-565 (2008).
32. Schuck, P., Perugini, M. A., Gonzales, N. R., Howlett, G. J., & Schubert, D. Size-distribution analysis of proteins by analytical ultracentrifugation: strategies and application to model systems. *Biophys. J.* 82, 1096-1111 (2002).
33. Laue, T. M., Shah, B. D., Ridgeway, T. M., & Pelletier, S. L. Computer-aided interpretation of analytical sedimentation data for proteins in *Analytical Ultracentrifugation in Biochemistry and Polymer Science* (eds. Harding, S. E., Horfon, J. C. & Rowe, A. J.) 90-125 (Royal Society of Chemistry, Cambridge, 1992).
34. McDonald, J. M. et al. The presence of sodium dodecyl sulphate-stable A beta dimers is strongly associated with Alzheimer-type dementia. *Brain* 133, 1328-1341 (2010).
35. Bueler, H. et al. Normal development and behaviour of mice lacking the neuronal cell-surface PrP protein. *Nature* 356, 577-582 (1992).
36. Klyubin, I. et al. Amyloid beta protein dimer-containing human CSF disrupts synaptic plasticity: prevention by systemic passive immunization. *J. Neurosci.* 28, 4231-4237 (2008).
37. Jackson, G. S. et al. Multiple folding pathways for heterologously expressed human prion protein. *Biochim. Biophys. Acta* 1431, 1-13 (1999).
38. Zahn, R., von Schroetter, C. & Wuthrich, K. Human prion proteins expressed in *Escherichia coli* and purified by high-affinity column refolding. *FEBS Lett.* 417, 400-404 (1997).
39. Soini, E. & Kojola, H. Time-Resolved Fluorometer for Lanthanide Chelates—A New Generation of Non-Isotopic Immunoassays. *Clin. Chem.* 29, 65-68 (1983).

---

What is claimed is:

1. A method of treating Alzheimer's Disease in a subject, the method comprising administering to the subject a therapeutically effective amount of an-anti-prion protein (anti-PrP) antibody having the complementarity determining sequences (CDRs) DYNLD (amino acids 50 to 54 of SEQ ID NO:4), NVYPNNGVTGYNQKFRG (amino acids 69 to 85 of SEQ ID NO:4), YYYDVSY(amino acids 118 to 124 of SEQ ID NO:4), SASSSVSYMH (amino acids 46 to 55 of SEQ ID NO:6), DTSKLAS (amino acids 71 to 77 of SEQ ID NO:6), and HQWRSNPYT (amino acids 110 to 118 of SEQ ID NO:6) which specifically binds an epitope of human PrP within amino acids 109 to 131 of SEQ ID NO: 2.

2. The method of claim 1, wherein the antibody is a monoclonal antibody, humanized antibody, chimeric antibody, scFv, Fab or other antigen binding fragment thereof.

3. The method of claim 2, wherein the monoclonal antibody is ICSM 18, a humanized form thereof, or an antigen binding fragment thereof.

4. The method of claim 2, wherein the monoclonal antibody is ICSM 18, or a humanized form thereof.

5. The method of claim 1, further comprising administering an additional therapeutic agent.

6. The method of claim 1, wherein the antibody is an immunoglobulin (Ig)G, IgE, IgM, IgD, IgA, or IgY.

7. The method of claim 6 wherein the antibody is an IgG1, IgG2, IgG3, IgG4, IgA1 or IgA2.

8. The method of claim 1, wherein the antibody binds PrP at a site within amino acid residues 131 to 153 of PrP with an affinity of 100 nM or less.

9. The method of claim 1 wherein the antibody comprises SEQ ID NO: 4 and SEQ ID NO: 6.

10. The method of claim 1, wherein the anti PrP antibody is administered at a dosage ranging from 0.0001 to 100 mg/kg.

11. The method of claim 1, wherein the subject is a human subject.

12. The method of claim 1, wherein the antibody is administered by subcutaneous injection, intravenously, by injection or infusion into the cerebrospinal fluid (CSF) or intracerebrally.

13. A method of inhibiting suppression of long-term potentiation in a subject, improving acute memory retention, improving spatial memory performance or improving acute memory retention and spatial memory performance, the method comprising
administering to a subject a therapeutically effective amount of an anti-PrP antibody having the complementarity determining sequences (CDRs) DYNLD (amino acids 50 to 54 of SEQ ID NO:4), NVYPNNGVTGYNQKFRG (amino acids 69 to 85 of SEQ ID NO:4), YYYDVSY(amino acids 118 to 124 of SEQ ID NO:4), SASSSVSYMH (amino acids 46 to 55 of SEQ ID NO:6), DTSKLAS (amino acids 71 to 77 of SEQ ID NO:6), and HQWRSNPYT (amino acids 110 to 118 of SEQ ID NO:6), which specifically binds an epitope of human PrP within amino acids 109 to 131 of SEQ ID NO: 2, wherein the subject has Alzheimer's Disease.

14. The method of claim 13, wherein the antibody is a monoclonal antibody, humanized antibody, chimeric antibody, scFv, Fab or other antigen binding fragment thereof.

15. The method of claim 14, wherein the monoclonal antibody is ICSM 18, a humanized form thereof, or an antigen binding fragment thereof.

16. The method of claim 14, wherein the monoclonal antibody is ICSM 18, or a humanized form thereof.

17. The method of claim 13, further comprising administering an additional therapeutic agent.

18. The method of claim 13, wherein the antibody is an IgG, IgE, IgM, IgD, IgA, or IgY.

19. The method of claim 18 wherein the antibody is an IgG1, IgG2, IgG3, IgG4, IgA1 or IgA2.

20. The method of claim 13, wherein the antibody binds PrP at a site within amino acid residues 131 to 153 of human PrP (SEQ ID NO: 1) with an affinity of 100 nM.

21. The method of claim 13, wherein the antibody comprises SEQ ID NO: 4 and SEQ ID NO: 6.

22. The method of claim 13, wherein the subject is a human subject.

23. The method of claim 13, wherein the antibody is administered by subcutaneous injection, intravenously, by injection or infusion into the cerebrospinal fluid (CSF) or intracerebrally.

24. The method of claim 13, wherein the anti PrP antibody is administered at a dosage ranging from 0.0001 to 100 mg/kg.

* * * * *